(12) United States Patent
Gladieux et al.

(10) Patent No.: US 11,786,278 B2
(45) Date of Patent: Oct. 17, 2023

(54) BONE ANCHOR INSERTION DEVICE AND METHODS OF USE

(71) Applicant: SeaSpine, Inc., Carlsbad, CA (US)

(72) Inventors: Corey Noel Gladieux, Carlsbad, CA (US); Leah Beyer Sherman, Carlsbad, CA (US); Hercules Frasier Walker, Carlsbad, CA (US)

(73) Assignee: SeaSpine, Inc., Carlsbad, CA (US)

( * ) Notice: Subject to any disclaimer, the term of this patent is extended or adjusted under 35 U.S.C. 154(b) by 0 days.

(21) Appl. No.: 17/687,254

(22) Filed: Mar. 4, 2022

(65) Prior Publication Data

US 2022/0280206 A1     Sep. 8, 2022

Related U.S. Application Data

(60) Provisional application No. 63/250,601, filed on Sep. 30, 2021, provisional application No. 63/157,281, filed on Mar. 5, 2021.

(51) Int. Cl.
    *A61B 17/70*      (2006.01)
    *A61B 17/88*      (2006.01)
    *A61B 17/00*      (2006.01)

(52) U.S. Cl.
    CPC ............ *A61B 17/7082* (2013.01); *A61B 2017/00407* (2013.01)

(58) Field of Classification Search
    CPC ............. A61B 17/7082; A61B 2017/00407
    USPC .................................. 606/86 A, 99, 104
    See application file for complete search history.

(56) References Cited

U.S. PATENT DOCUMENTS

| | | | |
|---|---|---|---|
| 2009/0254094 A1* | 10/2009 | Knapp | A61B 17/1637 606/104 |
| 2014/0276894 A1 | 9/2014 | Ramsay et al. | |
| 2016/0030100 A1 | 2/2016 | Divincenzo et al. | |
| 2016/0135856 A1* | 5/2016 | Ramsay | A61B 17/7076 606/104 |
| 2018/0146990 A1 | 5/2018 | Manzanares et al. | |
| 2018/0353224 A1* | 12/2018 | Kam | A61B 17/7082 |
| 2018/0368893 A1* | 12/2018 | DiVincenzo | A61B 17/1604 |
| 2019/0125421 A1* | 5/2019 | Smith | A61B 17/8875 |
| 2019/0183516 A1* | 6/2019 | Peterson | A61B 17/1757 |
| 2020/0093530 A1 | 3/2020 | Klausman et al. | |
| 2020/0121397 A1* | 4/2020 | Elliott | A61B 34/20 |
| 2020/0390478 A1* | 12/2020 | Rodriguez | A61B 17/7001 |

OTHER PUBLICATIONS

International Searching Authority; International Search Report and Written Opinion issued in Application No. PCT/US2022/018966; 11 pages; dated Jun. 20, 2022.

\* cited by examiner

*Primary Examiner* — Eduardo C Robert
*Assistant Examiner* — David C Comstock
(74) *Attorney, Agent, or Firm* — Dinsmore & Shohl LLP

(57) ABSTRACT

A bone anchor insertion device for delivering one or more bone anchor components into bone is provided. The insertion device improves surgical control in bone anchor location, placement and insertion into target bone. The bone anchor insertion device also improves efficiency in placing the bone anchor. The surgical instrument provides improved control of stylet location and orientation, including directional control for precise bone anchor component insertion. Methods to use the bone anchor insertion device in surgical procedures are also provided.

20 Claims, 29 Drawing Sheets

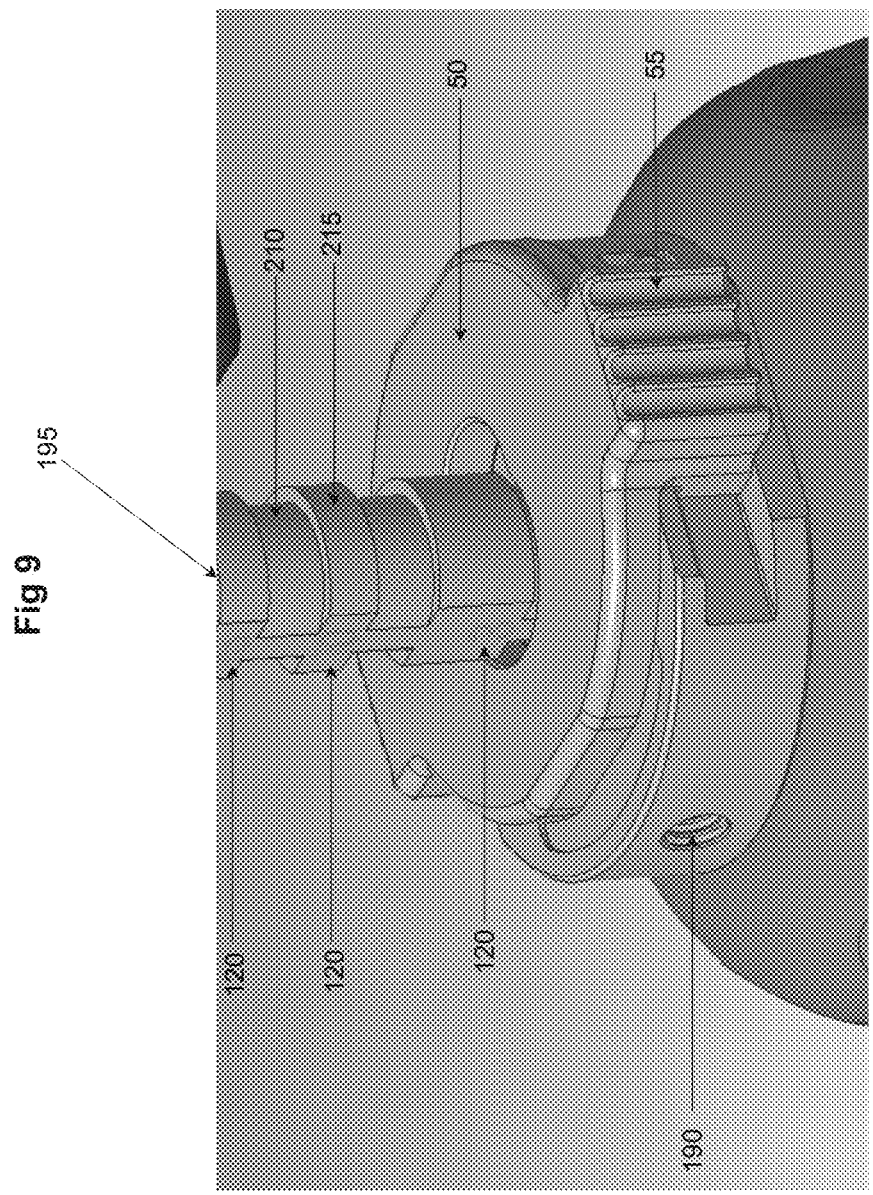

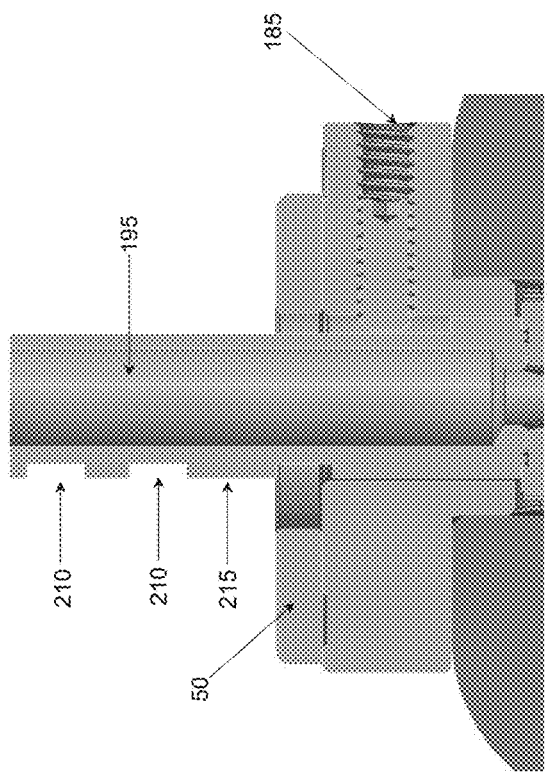
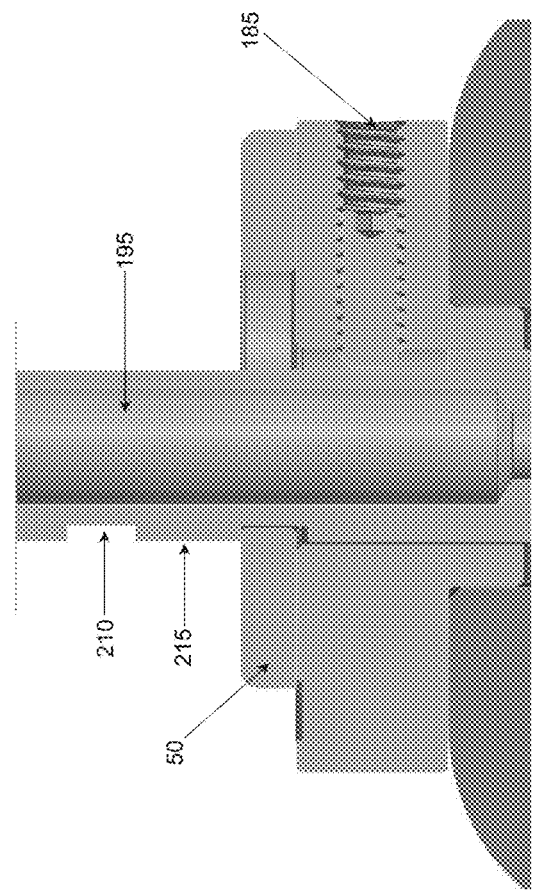

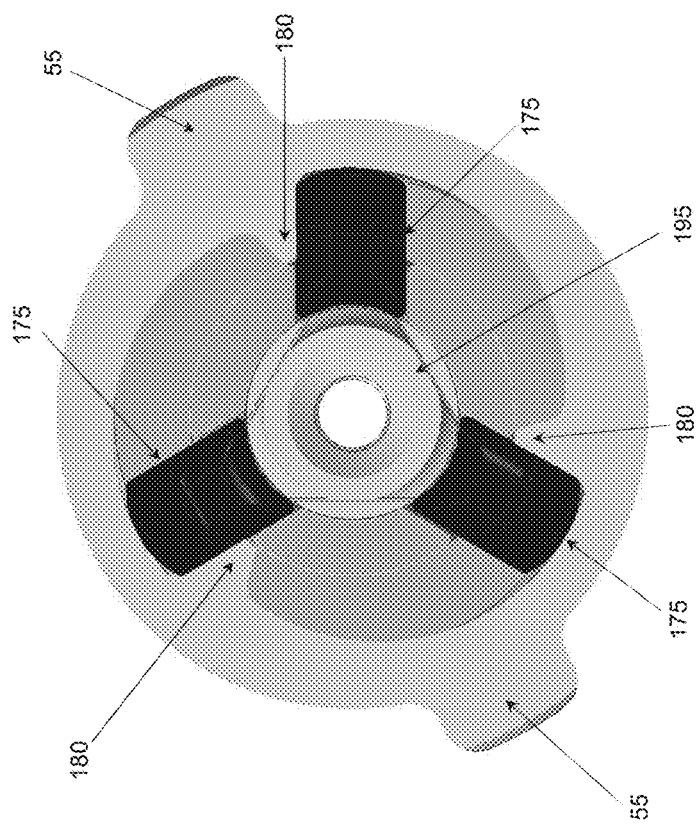
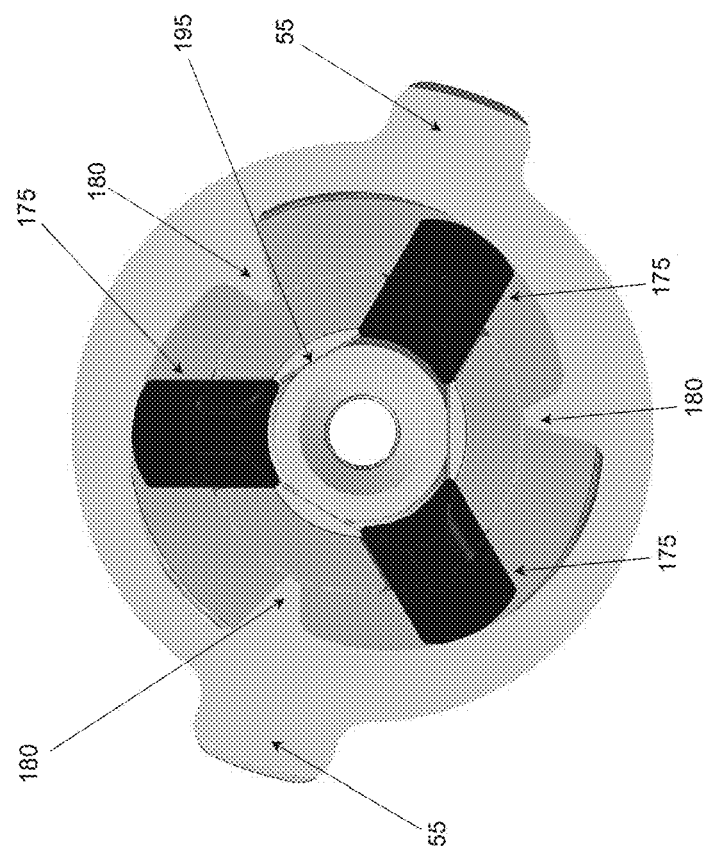

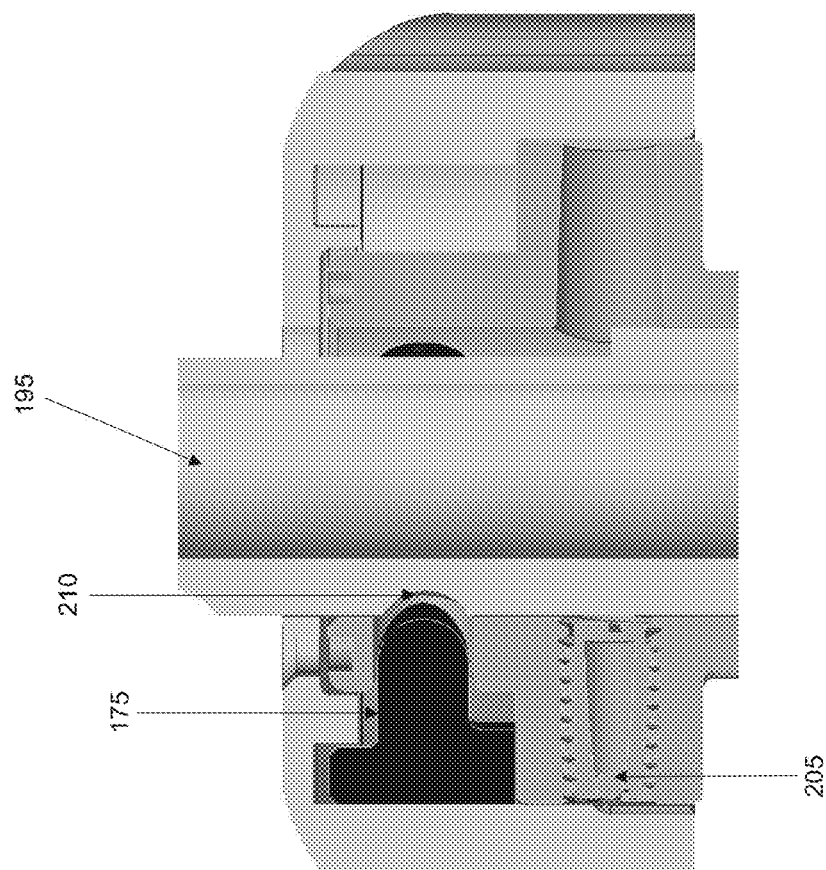
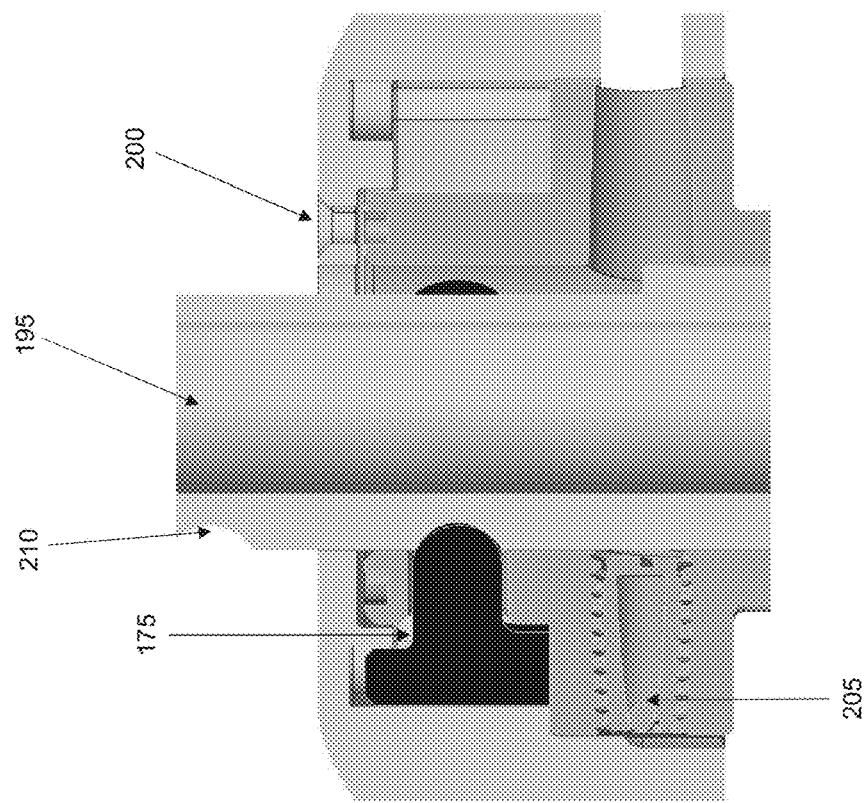

BONE ANCHOR INSERTION DEVICE AND METHODS OF USE

CROSS-REFERENCE TO RELATED APPLICATIONS

This application is a nonprovisional patent application of and claims priority to and benefit under 35 U.S.C. § 119 to U.S. Provisional Application No. 63/157,281, filed Mar. 5, 2021, and U.S. Provisional Application No. 63/250,601, filed Sep. 30, 2021. The entire contents of the aforementioned applications are herein incorporated by reference in their entirety.

FIELD OF THE INVENTION

The present disclosure provides a bone anchor insertion device and methods of use. The device is particularly advantageous in that it streamlines surgical workflow to reduce surgical operation time, while providing optimum intraoperative feedback, greater tactile feel and surgeon control when using the device to insert a bone anchor into the target bone site of a patient.

BACKGROUND

Spinal surgeries are typically employed to treat spinal conditions that result when functional segmental units of the spine are improperly aligned or otherwise damaged. Example spinal surgical procedures to treat spinal conditions include disc replacement, laminectomies, spinal fusion, and the like.

One aspect of certain spinal procedures, such as spinal fusion, is to stabilize the spine by preventing movement between the vertebrae while the bones of the spine heal. Such stabilization of the spine by securing the relevant bones during the healing process has greatly improved the success rate of spinal fusions and other procedures.

With spinal stabilization procedures, a combination of metal screws and rods may be used to create a bracing structure that holds the vertebrae in place. These devices are intended to stop movement from occurring between the vertebrae. These stabilization components provide greater stability to the fusion site and allow the patient to be ambulatory much sooner.

In spinal surgery, for example, bone anchors can be used to secure a spinal fixation element to one or more vertebrae to rigidly or dynamically stabilize the spine in order to promote healing and potentially increased mobility for the patient.

During the spinal stabilization procedure, pedicle screws are typically placed through the pedicles on the posterior portion of two or more vertebrae of the spinal column. The screws grab into the bone of the vertebral bodies, providing a secure hold on the vertebrae. Once the screws are placed on the vertebrae, they are attached to metal rods that connect all the screws together, producing an assembly that creates a stiff metal frame that holds the vertebrae so that healing can occur.

Surgeons also desire to minimize the amount of operation duration and post-surgical recovery time, in order to minimize trauma to the patient's spine and to facilitate faster healing. A recurrent desire is to produce spinal surgery tools which speed the surgical operation time, in addition to providing increased control and feel using the relevant surgical tools for the surgeon during the procedure.

The following disclosed device helps to meet these desired device configurations and uses.

SUMMARY

In an embodiment, a bone anchor insertion device comprises a proximal section comprising an impact-receiving region; a distal section comprising a handle, wherein the distal section interfaces with the proximal section; a driver, wherein the driver interfaces with the distal section; and a stylet; wherein the stylet resides in a channel extending from the proximal section through the distal section and through the driver, and the proximal section translates without rotation relative to the distal section.

In another embodiment, a bone anchor insertion device described herein comprises a proximal section and a distal section that are fixedly interconnected.

In still another embodiment, a bone anchor insertion device described herein comprises a proximal section and a distal section that are removably interconnected.

In yet another embodiment, a bone anchor insertion device described herein comprises a driver that is removably interconnected to the distal section.

In an embodiment, a bone anchor insertion device described herein comprises a driver that is fixedly interconnected to the distal section.

In another embodiment, a bone anchor insertion device described herein comprises a driver that removably engages a bone anchor assembly, a screw, a shank, a tulip, or a combination thereof.

In still another embodiment, a bone anchor insertion device described herein comprises a retractable stylet.

In an embodiment, a bone anchor insertion device described herein comprises a stylet with a beveled tip or a pointed tip.

In yet another embodiment, a bone anchor insertion device described herein comprises a stylet in which the stylet direction is rotatably controlled.

In an embodiment, a bone anchor insertion device described herein comprises a distal section that further comprises a lock to fix the protrusion distance of the stylet from the distal end of the driver.

In another embodiment, a bone anchor insertion device described herein comprises a stylet that is removably housed in the channel.

In still another embodiment, a bone anchor insertion device described herein comprises a stylet that is fixedly housed in the channel.

In yet another embodiment, a bone anchor insertion device described herein has a distal section that further comprises a spring, piston, hydraulic component, an elastic component, a magnetic component, or any combination thereof.

In an embodiment, a bone anchor insertion device described herein has a distal section that further comprises a collar.

In a further embodiment, a bone anchor insertion device described herein has a collar that further comprises a lock.

In another embodiment, a bone anchor insertion device described herein has a handle which further comprises a ratcheting mechanism.

In yet another embodiment, a bone anchor insertion device is described herein, wherein the handle is axially rotatable.

In still another embodiment, a bone anchor insertion device is described herein, wherein the stylet further comprises a cap.

In a further embodiment, a bone anchor insertion device comprises a proximal section comprising an impact-receiving region; a distal section comprising a handle, wherein the distal section interfaces with the proximal section; a driver, wherein the driver interfaces with the distal section; and a retractable stylet, wherein the stylet resides in a channel extending from the proximal section through the distal section and through the driver, and the proximal section translates without rotation relative to the distal section.

In an embodiment, a bone anchor insertion device comprises a proximal section comprising an impact-receiving region; a distal section comprising a handle, wherein the distal section interfaces with the proximal section; a driver, wherein the driver interfaces with the distal section; and a stylet, wherein the stylet resides in a channel extending from the proximal section through the distal section and through the driver, the stylet is rotatably controlled, and the proximal section translates without rotation relative to the distal section.

In an embodiment, a bone anchor insertion device comprises a proximal section comprising an impact-receiving region; a distal section comprising a handle, wherein the distal section interfaces with the proximal section; a driver, wherein the driver is fixedly interconnected to the distal section; and a retractable stylet; wherein the stylet resides in a channel extending from the proximal section through the distal section and through the driver, and the proximal section translates without rotation relative to the distal section.

In an embodiment, a bone anchor insertion device comprises a proximal section comprising an impact-receiving region; a distal section comprising a handle, wherein the distal section interfaces with the proximal section; a driver, wherein the driver is removably interconnected to the distal section; and a retractable stylet; wherein the stylet resides in a channel extending from the proximal section through the distal section and through the driver, and the proximal section translates without rotation relative to the distal section.

In another embodiment, a bone anchor insertion device comprises a proximal section comprising an impact-receiving region; a distal section comprising a handle, wherein the distal section interfaces with the proximal section; a driver, wherein the driver interfaces the said distal section; a shuttle; and a stylet; wherein the shuttle engages with the proximal section to control rotation and translation of the stylet.

In an embodiment, a method for inserting an anchor device into bone comprises providing a bone anchor insertion device comprising a proximal section comprising an impact-receiving region; a distal section comprising a handle, wherein the distal section interfaces with the proximal section; a driver, wherein the driver interfaces with the distal section; and a stylet; wherein the stylet resides in a channel extending from the proximal section through the distal section and through the driver, and the proximal section translates without rotation relative to the distal section; creating an access opening to expose a target bone insertion site; positioning the distal tip of the stylet of the bone anchor insertion device at a desired point on the target bone; impacting the proximal portion of the bone anchor insertion device; extending the stylet of the bone anchor insertion device; rotating the handle of the bone anchor insertion device and driving the bone anchor component into the target bone site; retracting the stylet from the target bone site; inserting an anchor device into the target bone insertion site; and disengaging the bone anchor insertion device from the anchor device.

In another embodiment, a method is disclosed for inserting an anchor device into bone comprising positioning a distal tip of an insertion device on a target bone; impacting a proximal portion of the insertion device to drive a stylet into the target bone; rotating a handle of the insertion device to threadedly drive the anchor device into the target bone; retracting the stylet from the target bone; inserting an anchor device into the target bone; and disengaging the bone anchor insertion device from the anchor device.

In a further embodiment, a method for inserting a cannulated screw into bone comprises coupling (or mating, engaging, associating, or interfacing) a cannulated screw with a distal end of an insertion device; positioning the distal tip of the cannulated screw on a target bone; impacting a proximal portion of the insertion device to drive a stylet into the target bone; rotating a handle of the insertion device to threadedly drive the cannulated screw into the target bone; retracting the stylet from the target bone; inserting a cannulated screw into the target bone; aspirating bone marrow from the bone through the cannulated screw and insertion device; and disengaging the insertion device from the cannulated screw.

BRIEF DESCRIPTION OF THE FIGURES

FIG. 9 is a closeup perspective view of a proximal section of an example bone anchor insertion device illustrating a sliding collar in an unlocked position.

FIG. 10a is a closeup view of a sliding collar lock in the engaged (locked) position of an example bone anchor insertion device.

FIG. 10b is a closeup view of a sliding collar lock in the disengaged (unlocked) position of an example bone anchor insertion device.

FIG. 11a is an internal top view of a collar lock in the disengaged (unlocked) position of an example bone anchor insertion device.

FIG. 11b is an internal top view of a lock in the engaged (locked) position of an example bone anchor insertion device.

FIG. 12a is a cutaway side view of a collar lock in the engaged (locked) position of an example bone anchor insertion device.

FIG. 12b is a cutaway side view of a collar lock in the disengaged (unlocked) position of an example bone anchor insertion device.

DETAILED DESCRIPTION

Figure 1A:
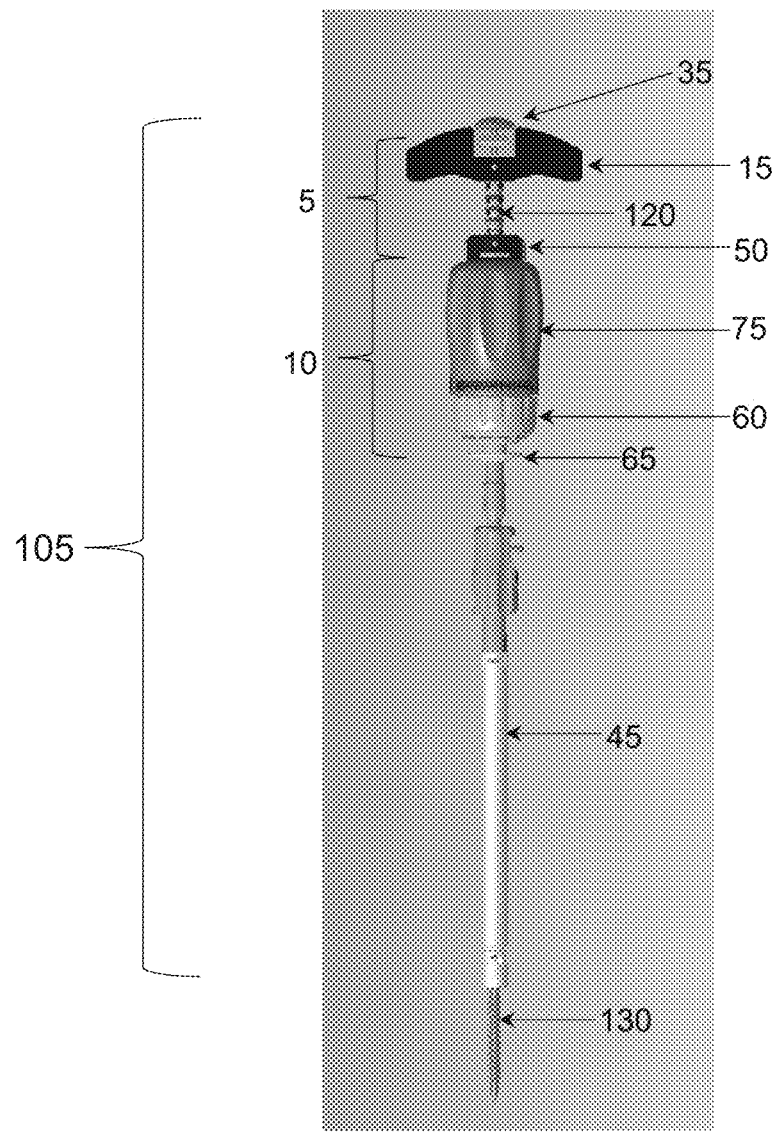
FIG. 1a is a view of an example bone anchor insertion device.

Certain exemplary embodiments ("examples", "embodiments", etc.) are described to provide an overall understanding of the principles of the function, structure, manufacture, use and preparation of the devices and methodology disclosed herein. While one or more embodiments and/or examples are described and illustrated in the accompanying drawings, one of ordinary skill in the relevant art will readily understand that the devices, processes, methods of use, relevant drawings, etc. specifically described herein are non-limiting exemplary embodiments and that the scope of the invention is defined by the accompanying claims in this disclosure. The features described, illustrated or exemplified with one or more embodiments may also be combined with the features of one or more other examples or embodiments. Such combinations, modifications, and variations are included within the scope of the presently described invention. One of ordinary skill in the art will appreciate and readily understand that the devices disclosed herein can have various configurations in addition to the examples and embodiments disclosed herein, and that the various features as disclosed herein in the various embodiments are interchangeable and able to be combined.

In general, various insertion instruments are provided for driving a bone anchor device or bone anchor assembly into bone. The insertion instruments generally include a handle assembly and an elongate driver extending distally therefrom for coupling to a bone anchor assembly. The instruments are configured to receive a stylet therethrough and the handle assembly is configured to control positioning of the stylet. In particular, the handle assembly can be configured to allow for adjustment of an axial position of the stylet relative to a bone anchor assembly coupled to the driver. The handle assembly can also be configured to move the stylet proximally relative to a bone anchor assembly during insertion of the bone anchor assembly into bone. One skilled in the art will appreciate that the instruments disclosed herein can have a variety of configurations, and that the various features disclosed in the various embodiments are interchangeable. Generally, the bone anchor insertion device provides a proximal portion interfaced with a distal section, which is in turn engaged with a driver. The driver ultimately engages the bone anchor of various configurations that is to be placed into the target bone of the patient. A stylet resides in a lumen passing from the proximal section, through the distal section, and through the driver to ultimately emerge from the distal tip of the driver. In one or more embodiments, the distance that the stylet emerges from the distal tip of the driver is controlled by the user, and is easily controlled with reference to a depth indicator included in the proximal section of the bone anchor insertion device.

Exemplary embodiments described herein provide an overall understanding of the principles of the structure, function, manufacture, and use of the devices and methods disclosed herein. One or more examples of these embodiments are illustrated in the accompanying drawings. One of skill in the art will understand that the devices and methods described herein and illustrated in the accompanying drawings are non-limiting exemplary embodiments Features illustrated and/or described in connection with one exemplary embodiment may be combined with the features of one or more other embodiments; such modifications and variations are intended to be included within the scope of the present invention.

Methods and devices for inserting bone anchor devices and/or bone anchor assemblies into bone are provided herein. Use of these anchors or instruments can eliminate one or more of the steps in a conventional bone anchor installation procedure, improving surgical efficiency and patient safety.

One general advantage of the present device is significantly reduced surgery time spent in the operating room. Another advantage is that multiple steps of inserting a bone anchor into a target bone site using multiple surgical tools are reduced by combining breaching cortical bone, confirmation of the desired trajectory, and insertion of a bone anchor using a single device. Another advantage is that the present impaction-based device allows a surgeon's tactile feel using the bone anchor insertion device, which is a significant advantage over conventional devices that do not afford such tactile feel in operating a bone anchor insertion device. The present device is also more intuitive for ease of use and eliminates the necessity of a guide wire for bone anchor insertion. The adjustable length of the stylet for insertion of one or more bone anchors into target bone through impaction-based preparation of a bone target site is clearly differentiated from conventional devices that use rotational movement.

The following detailed description provides further disclosure with reference to the accompanying drawings.

FIGS. 1a to 1h, 2a to 2b, 3, 4a to 4d, 5, 6a to 6d, 7a to 7d, 8a to 8b, 9, 10a to 10b, 11a to 11b, and 12a to 12b provide one or more exemplary embodiments of a bone anchor insertion device (105) for driving a bone anchor device into bone. The bone anchor insertion device (105) includes a proximal section (5) configured to include a T-handle (15) disposed proximal to a depth indicator (120), along with an impaction cap (35) residing at the proximal end of the T-handle (15). A distal section (10) is interfaced with the proximal section (5), and the distal section (10) is configured to include a collar (50) disposed near the distal portion of the depth indicator (120), an axial handle (75) disposed at the distal end of the collar (50), and a ratchet (60) interfaced with the distal end of the axial handle (75). Collar (50) optionally includes a locking collar (55) that engages collar (50) to prevent axial rotation of collar (50) once locking collar (55) is engaged in the locked position.

Stylet (20) is engaged with, and extends distally from, T-handle (15). Stylet (20) further extends through proximal section (5) into and through distal section (10), continuing through driver (40) so that stylet tip (70) emerges from distal end of driver (40). Depth indicator (120) provides visual feedback to user regarding stylet tip (70) extension length from driver (40), and stylet (20) length allows stylet (20) to extend through and out the distal tip of an optionally engaged bone anchor device or bone anchor assembly, where the bone anchor device or bone anchor assembly is engaged by the distal tip of the driver (40).

Proximal section (5) and distal section (10) are configured to act together in driving a bone anchor device or bone anchor assembly into a target bone site. Proximal section (5) and distal section (10) are further configured to act together in manipulating stylet (20) and/or stylet tip (70) both before and during insertion of a bone anchor device or bone anchor assembly into target bone site. Manipulating stylet (20) includes, for example, depth adjustment of stylet (20) or stylet tip (70) into target bone and directionality of stylet tip (70). Stylet tip (70) examples include, but are not limited to, a bevel tip (100), a diamond tip (110), a trocar tip (115), and the like.

Driver (40) and optional driver sleeve (45) can have a variety of configurations; generally, driver (40) includes a proximal end for mating to the axial handle (75) through ratchet connector (65) and a distal end that facilitates mating to a bone anchor device or bone anchor assembly. The driver (40) length can vary; the driver (40) preferably is a length that allows the bone anchor insertion device (105) distal section (10) to be located outside of a patient's body while the distal portion of driver (40) is positioned into a patient's body adjacent to bone to facilitate insertion of a bone anchor device or bone anchor assembly into the target bone site.

Distal end of driver (40) is configured to mate to a bone anchor device or bone anchor assembly. For example, distal portion of driver (40) can include a threaded portion configured to engage corresponding threads formed in the receiver member of the bone anchor device or bone anchor assembly. In another example, a tip disposed distally of the threaded portion can be configured to engage a drive socket or a proximal surface of the bone anchor device or bone anchor assembly disposed within the receiving portion. A further example provides a tip having a diameter that is of smaller diameter than the threaded portion as described herein.

In FIG. 1a, an embodiment of bone anchor insertion device (105) is shown. In this embodiment, a proximal section (5) of the bone anchor insertion device (105) encompasses T-handle (15), impaction cap (35), and depth indicator (120). Impaction cap (35) provides a striking portion for a slap hammer or other impaction device, in order to drive stylet tip (70) into a target bone site. Distal section (10) is also shown in direct linear engagement with proximal section (5). In this representative embodiment, distal section (10) encompasses collar (50), axial handle (75), and ratchet (60). Axial handle (75) may alternatively be referred to as egg handle throughout this disclosure. Axial handle (75) in this representation is shown having a knurled grip. Without being limited by this example, axial handle (75) can alternatively have a different patterned grip texture, and may also be ergonomically shaped for comfort in handling the device.

Further in this FIG. 1a embodiment, ratchet connector (65) is shown engaged with driver sleeve (45), which in turn is engaged with driver (40). Driver tip (135) is shown in direct engagement with an example bone anchor (130), which in this example Figure is a bone anchor screw as illustrated. As one of ordinary skill in the art readily understands, other bone anchor devices may also be employed to engage with driver tip (135). Driver tip (135) housed within the distal end of driver sleeve (45) includes a variety of different tip configurations for engaging various anchor devices. For example, anchor devices include a polyaxial screw, a monoaxial screw, a uniplanar screw, a bone hook, and other known bone anchor devices or assemblies.

Figure 1B:
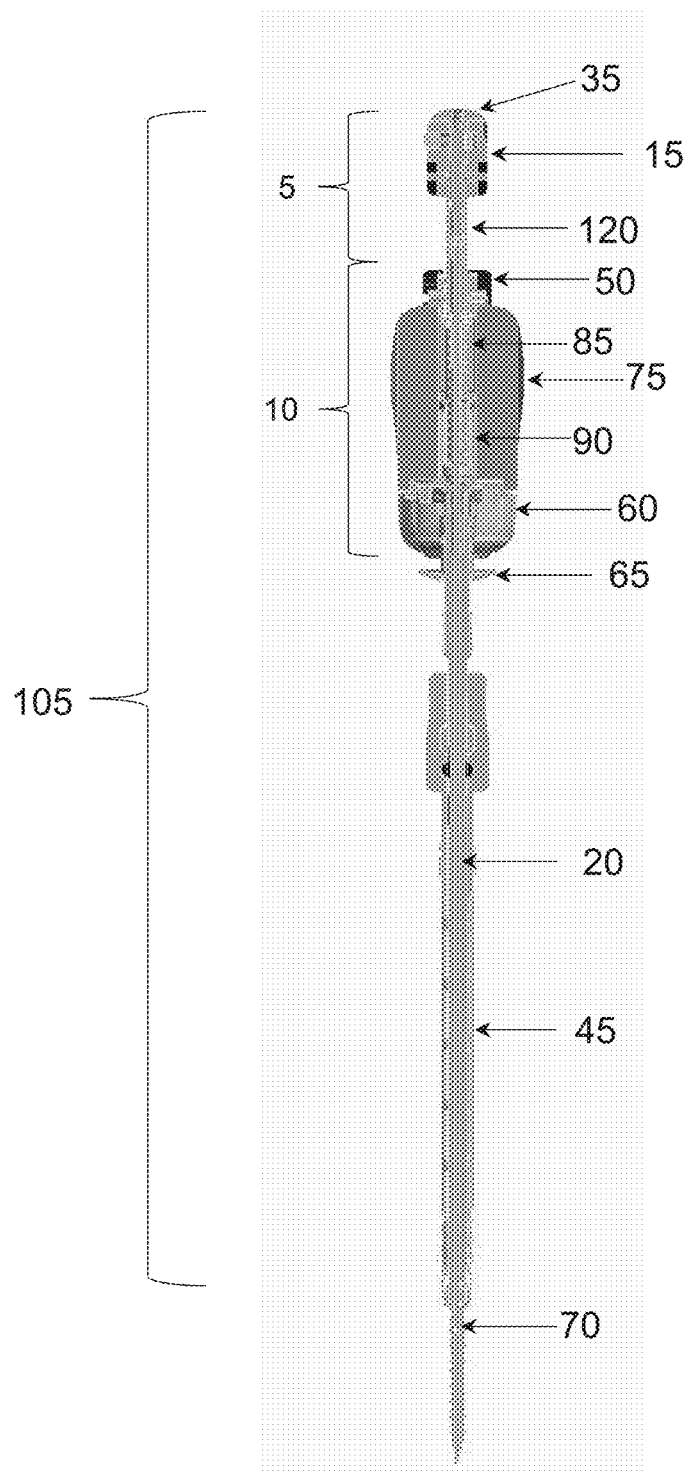
FIG. 1b is a cross-sectional view of an example bone anchor insertion device.

In FIG. 1b, an embodiment of bone anchor insertion device (105) is shown in a cross-sectional view. Similar to FIG. 1a, proximal section (5) encompasses T-handle (15), impaction cap (35), and depth indicator (120). Stylet (20) and corresponding stylet tip (70) are also illustrated. Stylet tip (70) is shown partially introduced into cannulated bone screw. Distal section (10) is shown in direct engagement with proximal section (5). In this embodiment, distal section (10) encompasses collar (50), axial handle (75), and ratchet (60). Handle spring (85) and threads (90) are illustrated within interior of axial handle (75). Ratchet connector (65) and driver sleeve (45) are also illustrated in this cross-sectional view of this embodiment.

Figure 1C:
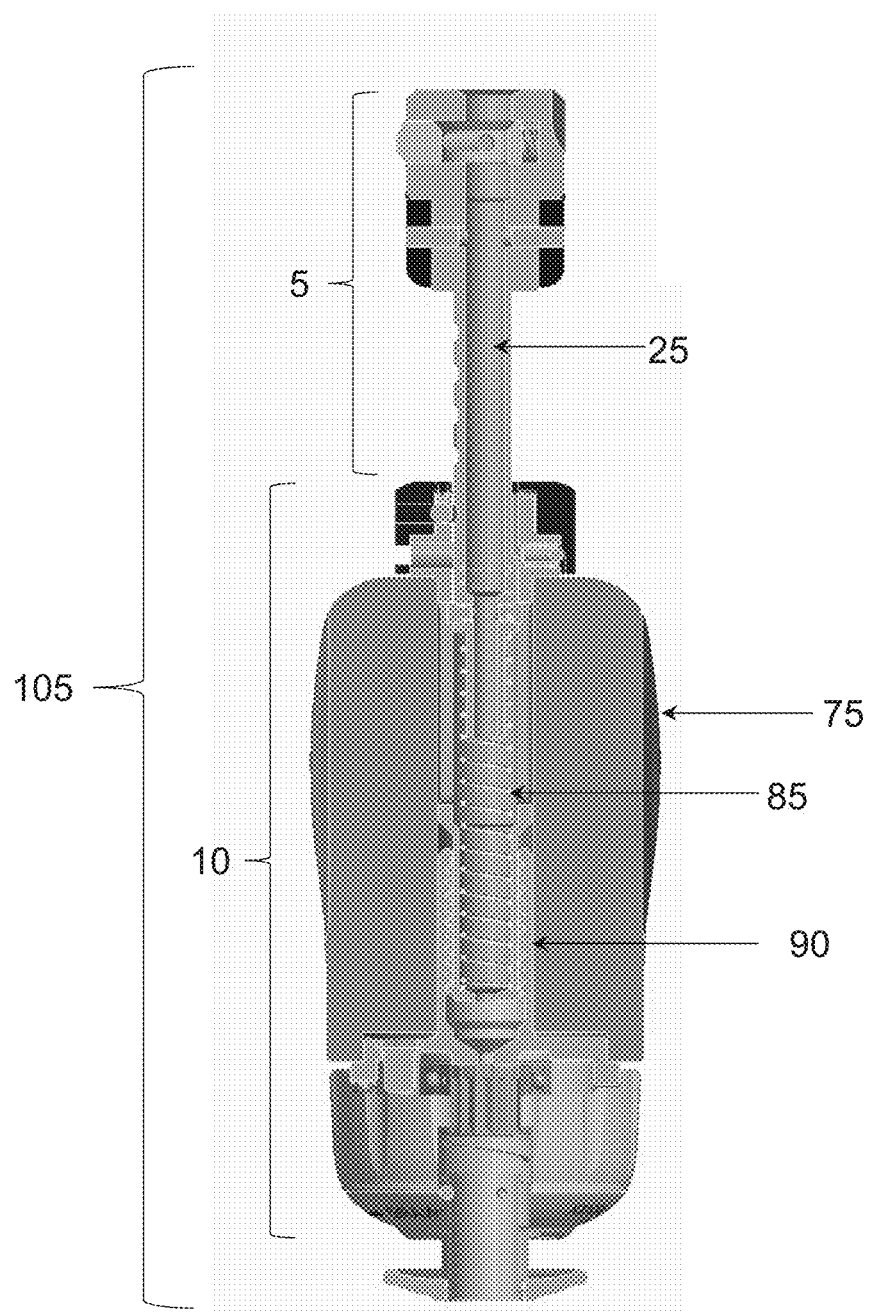
FIG. 1c is a close-up cross-sectional view of the proximal and distal sections of an example bone anchor insertion device.

In FIG. 1c, an embodiment of bone anchor insertion device (105) is illustrated in which a closeup view of proximal section (5) and distal section (10) are shown. Collar (50) is also illustrated in this embodiment. Handle spring (85) and threads (90) surrounding respective portions of shuttle (25) are shown in this embodiment residing within axial handle (75).

Figure 1D:
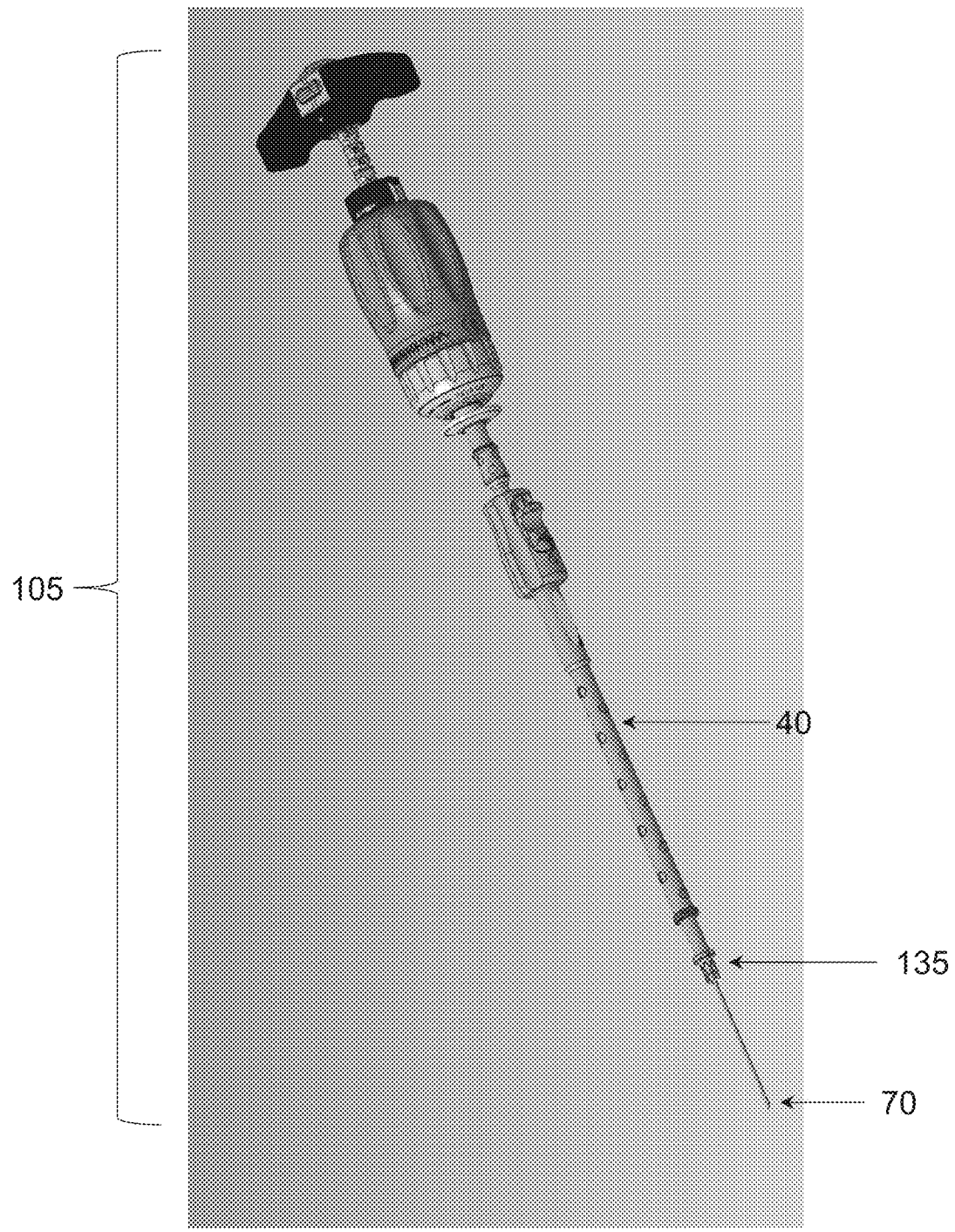
FIG. 1d is a perspective view of an example bone anchor insertion device with a visible extended stylet.

In FIG. 1d, an embodiment of assembled bone anchor insertion device (105) is shown. Stylet tip (70) is shown extending distally from driver (40) and also shows an example of exposed driver tip (135). Driver tip (135) may contain various means for bone anchor capture, including threads, and/or a male component that mates with an internal female component of an anchor, such as a hex head mating to a recessed hex void in bone anchor head portion. A torx, square, star patterned, or Philips head configuration in a bone anchor head portion may also mate to a corresponding male capture portion in the driver tip (135).

Figure 1E:
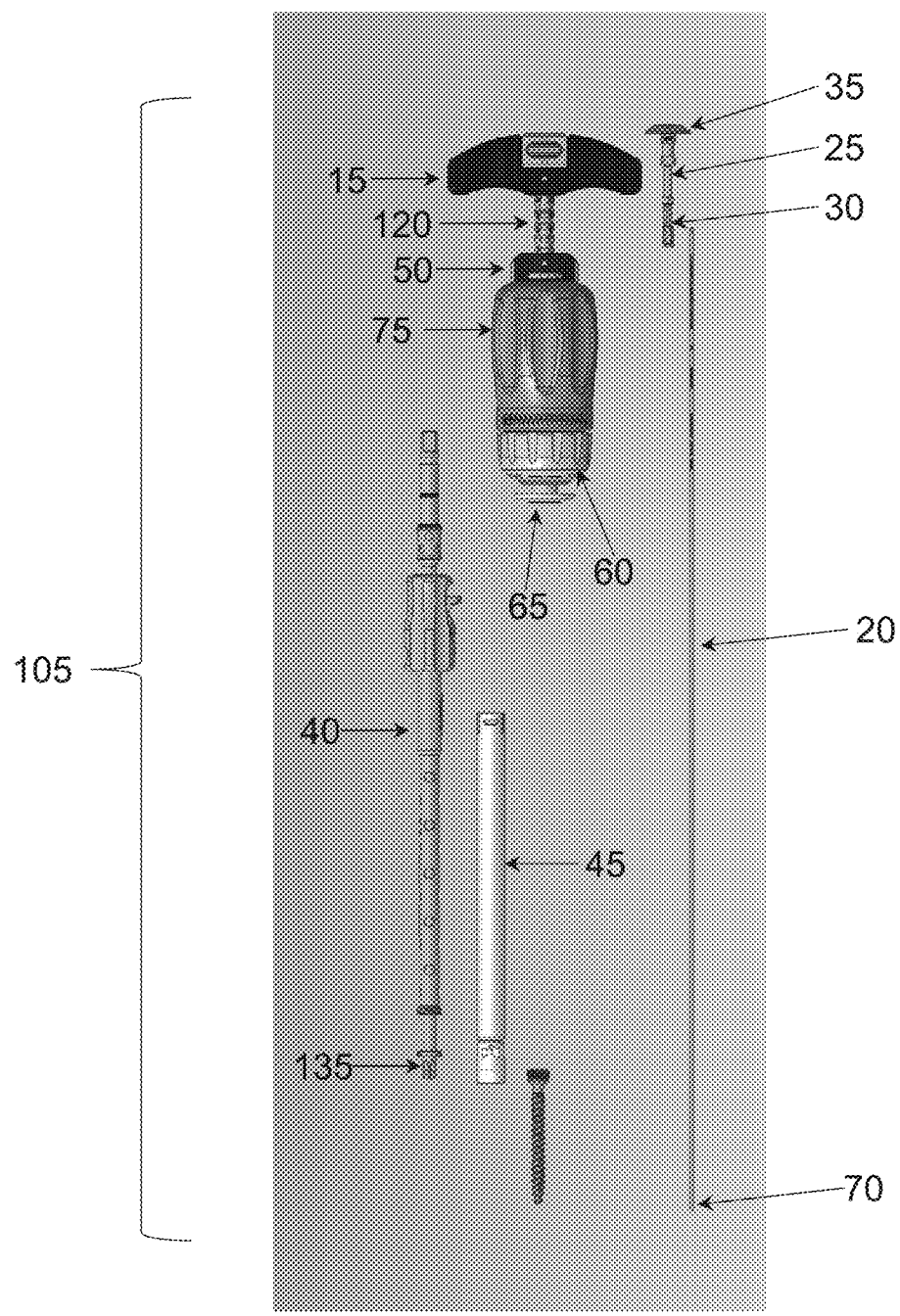
FIG. 1e is a view of a partially disassembled example bone anchor insertion device.

In FIG. 1e, an embodiment of bone anchor insertion device (105) is shown in partially disassembled state. T-handle (15), axial handle (75), depth indicator (120), ratchet (60), collar (50), shuttle (25) with impaction cap (35), shuttle cuff (30), stylet (20), stylet tip (70), driver (40), driver sleeve (45), and driver tip (135) are all illustrated. An example bone anchor device (screw) that may be used with the bone anchor insertion device is also shown for illustration purposes only. T-handle (15) engages with the proximal portion of depth indicator (120), and depth indicator can pass through collar (50) through axial handle (75). The proximal end of driver (40) engages with ratchet connector (65) to secure the desired driver for use by the surgeon. Various driver (40) proximal ends are compatible with ratchet connector (65), including square driver ends, and other patterned ends which mate with ratchet connector (65). When using stylet (20) in conjunction with driver (40), a lumen extends through driver (40) to allow passage of stylet (20) from proximal section through distal section and driver (40). Removable driver sleeve (45) houses distal portion of driver extending through to driver tip (135), with driver tip (135) housed in distal end of driver sleeve (45) when driver sleeve (45) is installed.

Figure 1F:
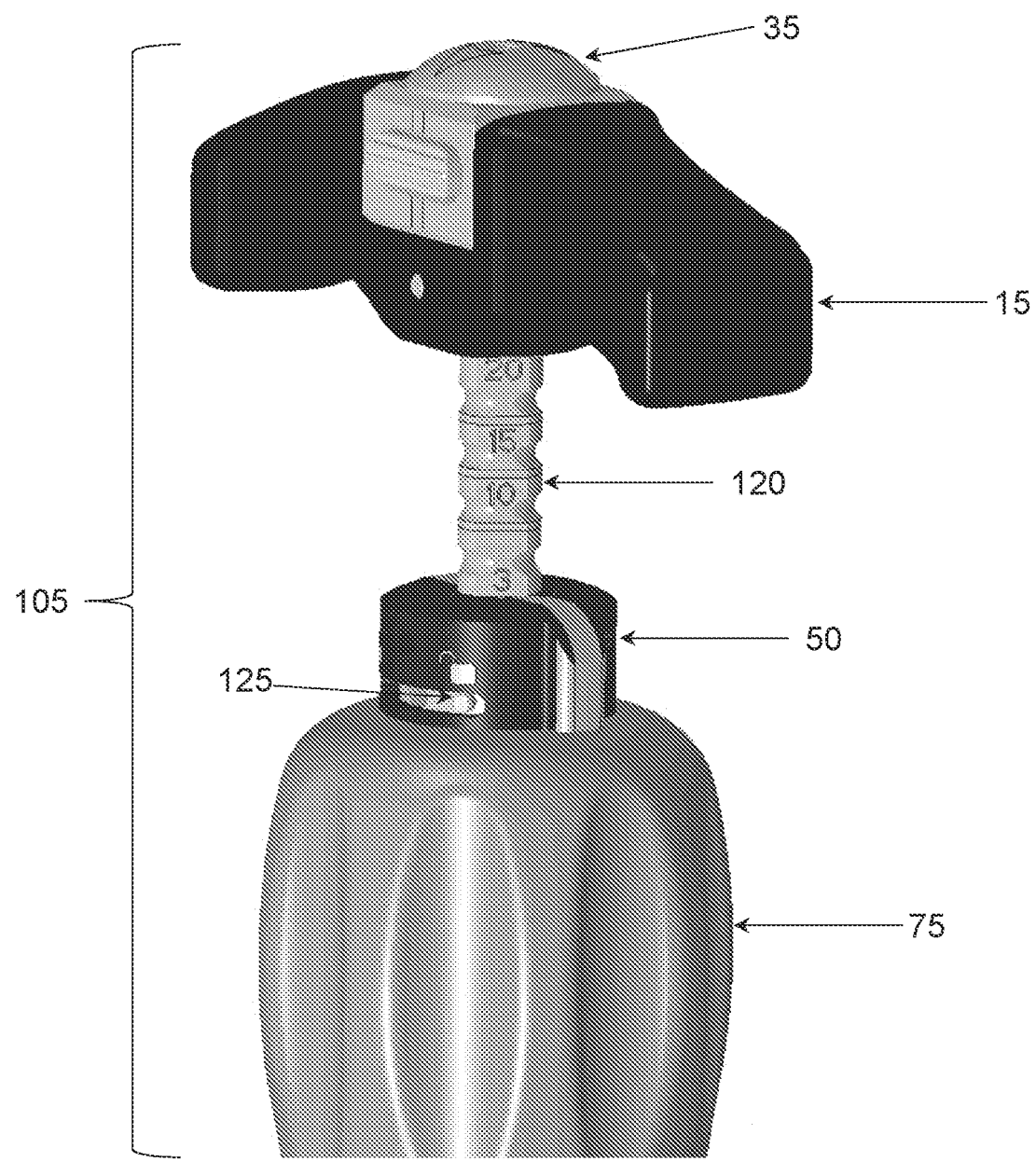
FIG. 1f is a close-up view of the proximal section and a portion of the distal section of an example bone anchor insertion device.

In FIG. 1f, an embodiment of bone anchor insertion device (105) is shown.

T-handle, axial handle (75), stylet lock (125), depth indicator (120), impaction cap (35), and collar (50) are also illustrated. T-handle (15) and axial handle (75) can include gripping features, such as a knurled outer surface, or other surface features formed thereon to facilitate grasping of the device. Knurled grip shown on axial handle (75) is one example, though other axial handle (75) textures may be included, such as a channeled grip, a fine patterned cross-weave pattern, a ribbed pattern, a stippled pattern, an irregular surface, and the like. Materials that may be used on the axial handle (75) grip include, inter alia, any metal, alloy, plastic, or combination thereof, along with other various materials that withstand autoclaving procedures.

Figure 1G:
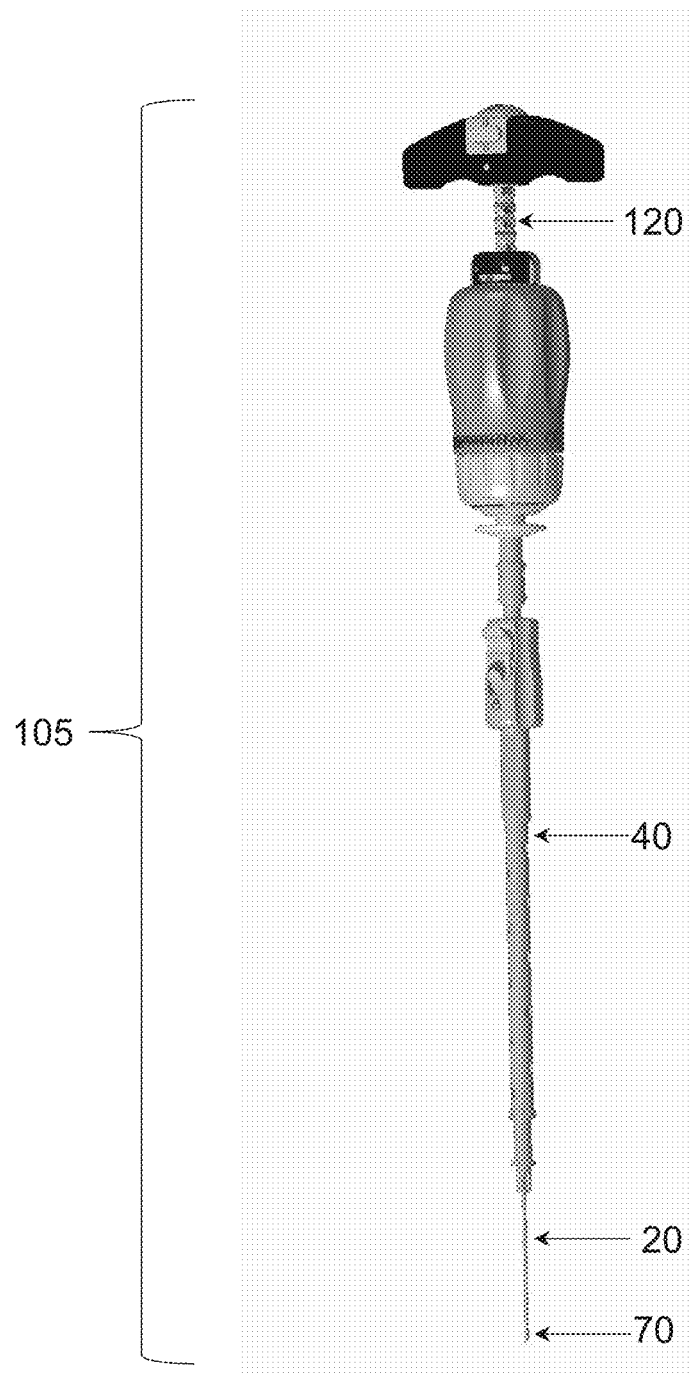
FIG. 1g is an alternative view of an example bone anchor insertion device.

In FIG. 1g, an embodiment of bone anchor insertion device (105) is shown. Stylet tip (70) is also shown to illustrate how stylet (20) extends distally from driver (40). In this embodiment, depth indicator (120) is also shown and indicates further extension of stylet tip (70) is still possible beyond the currently illustrated stylet tip (70) extension.

Figure 1H:
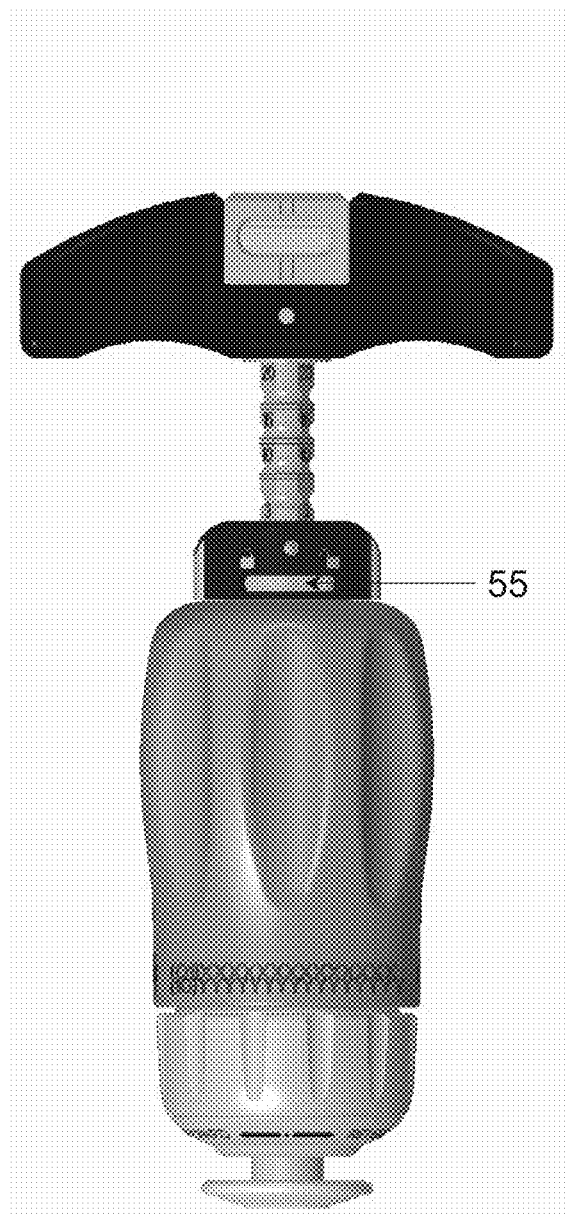
FIG. 1h is a closeup view of the proximal section and the distal section of an example bone anchor insertion device.

In FIG. 1h, an embodiment of bone anchor insertion device (105) is shown. Locking collar (55) is in the unlocked position in this Figure. When in the unlocked position, internal balls are free to sit in channels away for the translating proximal portion. When the lock is rotated into the locked positions, these balls are forced into the grooves on the proximal portion, obstructing translation. While locking collar (55) is shown as a rotatable raised portion in this embodiment, other locking collar configurations are also contemplated and included within this scope of the disclosure. For example, locking collar may be configured as a vertically oriented slidable lock, a horizontally oriented slidable lock, a movable latch, and the like.

Figure 2A:
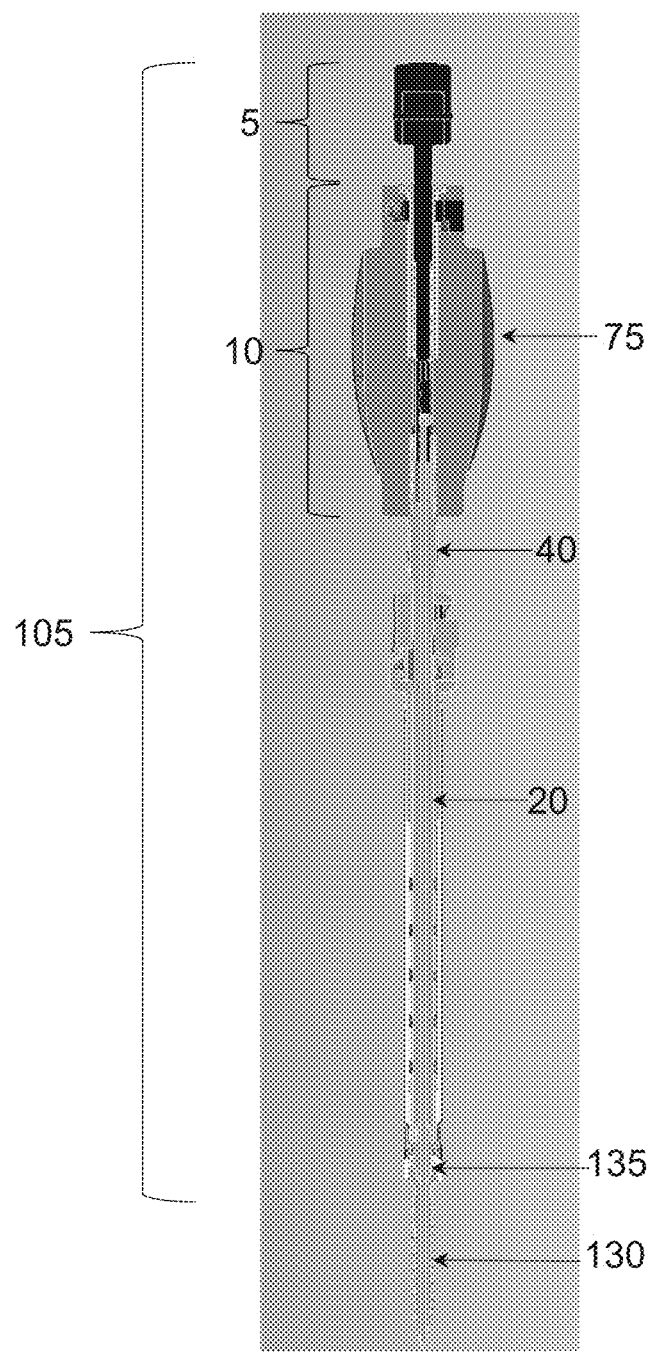
FIG. 2a is a cross-sectional view of an example bone anchor insertion device.

In FIG. 2a, a cross-sectional view of an embodiment of a bone anchor insertion device (105) is shown. In this embodiment, the driver (40) is fixedly attached to the distal portion (10) and directly interfaces with the axial handle (75). The proximal section (5) can translate without rotating relative to the distal portion (10) when fully engaged. When the button (155—not shown) is depressed, the proximal section (5) can disengage from the distal section (10). In this embodiment, the proximal section (5) engages the stylet (20) while the driver tip (135) is shown engaged to an example bone anchor (screw) (130). In this embodiment, handle spring (85—not shown) applies a retractive force to the proximal section (5).

Figure 2B:
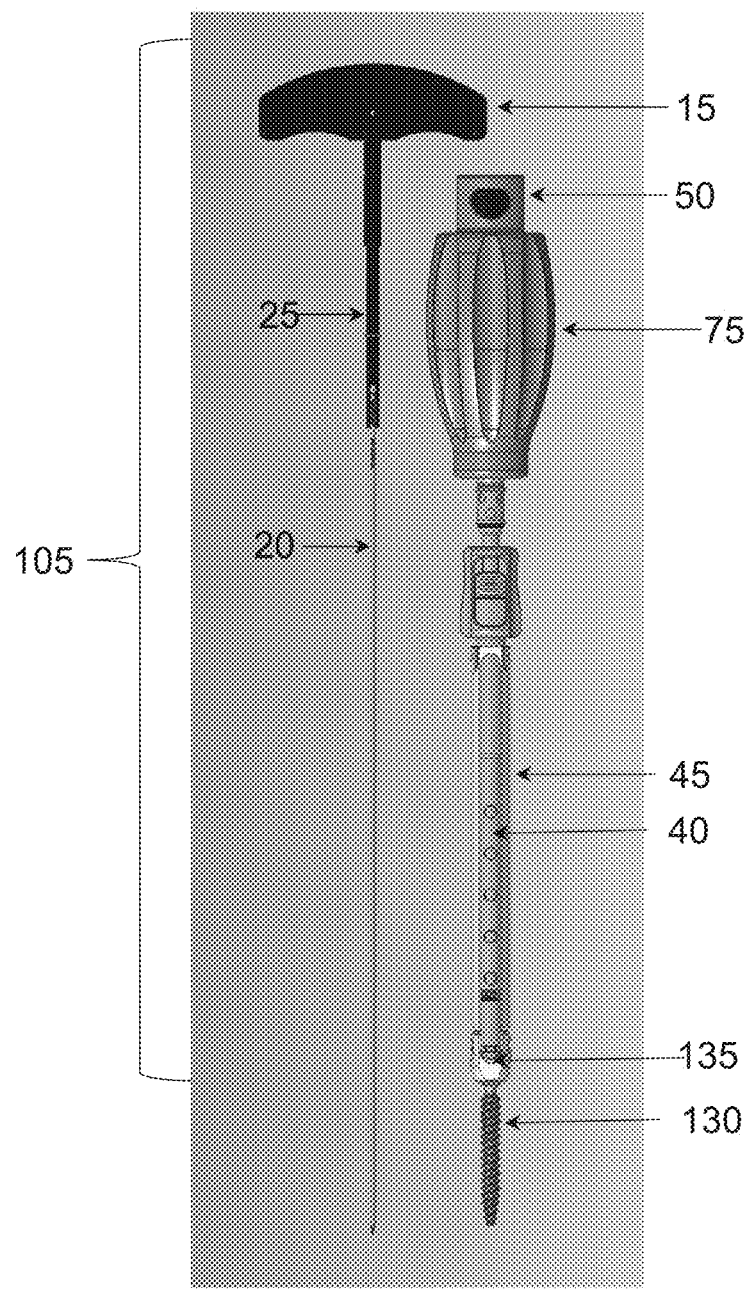
FIG. 2b is a view of an example bone anchor insertion device in a partially assembled state.

In FIG. 2b, an embodiment of a partially disassembled bone anchor insertion device (105) is shown. In this view, T-handle (15) is shown engaged with shuttle (25) and stylet (20). Also in this FIG. 2b, collar (50) is shown in contact with axial handle (75), which in turn engages driver sleeve (45) and driver (40), and an example bone anchor (130) is shown mated with driver tip (135). In one or more embodiments, T-handle (15) component coupled to shuttle (25) and stylet (20) are an integrated unit that may be modularly removed from the axial handle (75), driver sleeve (45) and driver (40) components, so a user may separately exchange a different stylet tip and/or stylet length for use in a relevant surgical procedure. One or more components of the bone anchor insertion device may be separately combined modular components, or may be fully integrated as a unitary device.

Figure 3:
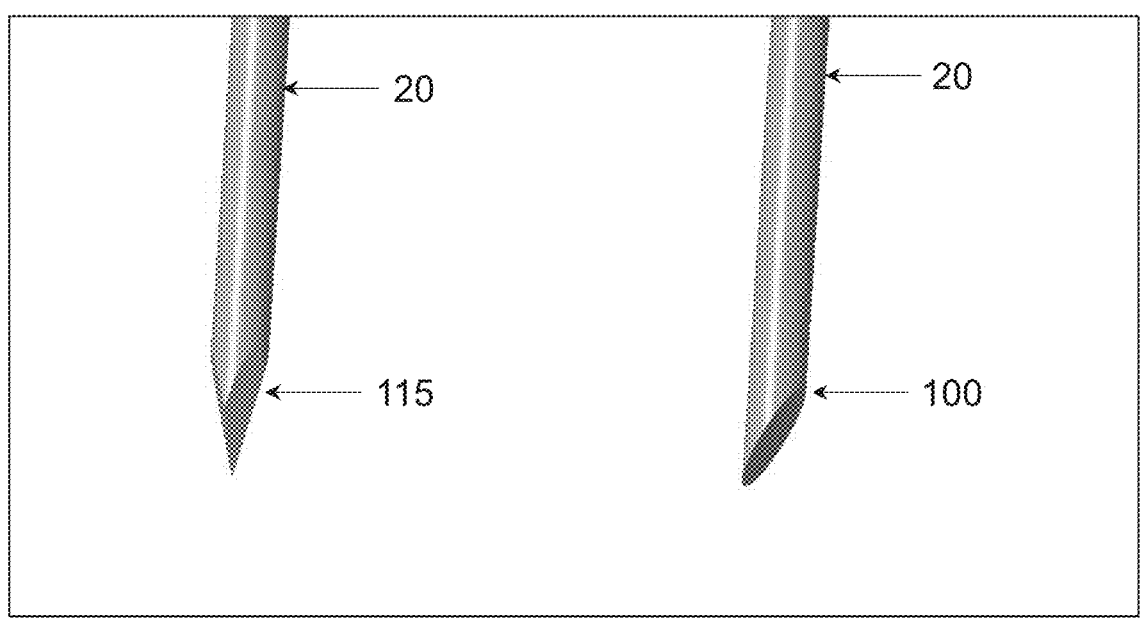
FIG. 3 is a closeup perspective view showing a trocar stylet tip (left) or a bevel stylet tip (right) of an example bone anchor insertion device.

In FIG. 3, two example stylet (20) configurations of an embodiment of bone anchor insertion device (105) are shown. Trocar tip (115) on the left side and bevel tip (100) on the right side illustrate different angles and orientation of tip directionality. As herein described, a user chooses a desired stylet tip (70) for the relevant target bone site and surgical procedural approach of the bone anchor insertion. Other stylet tip configurations may also be employed.

Figure 4A:
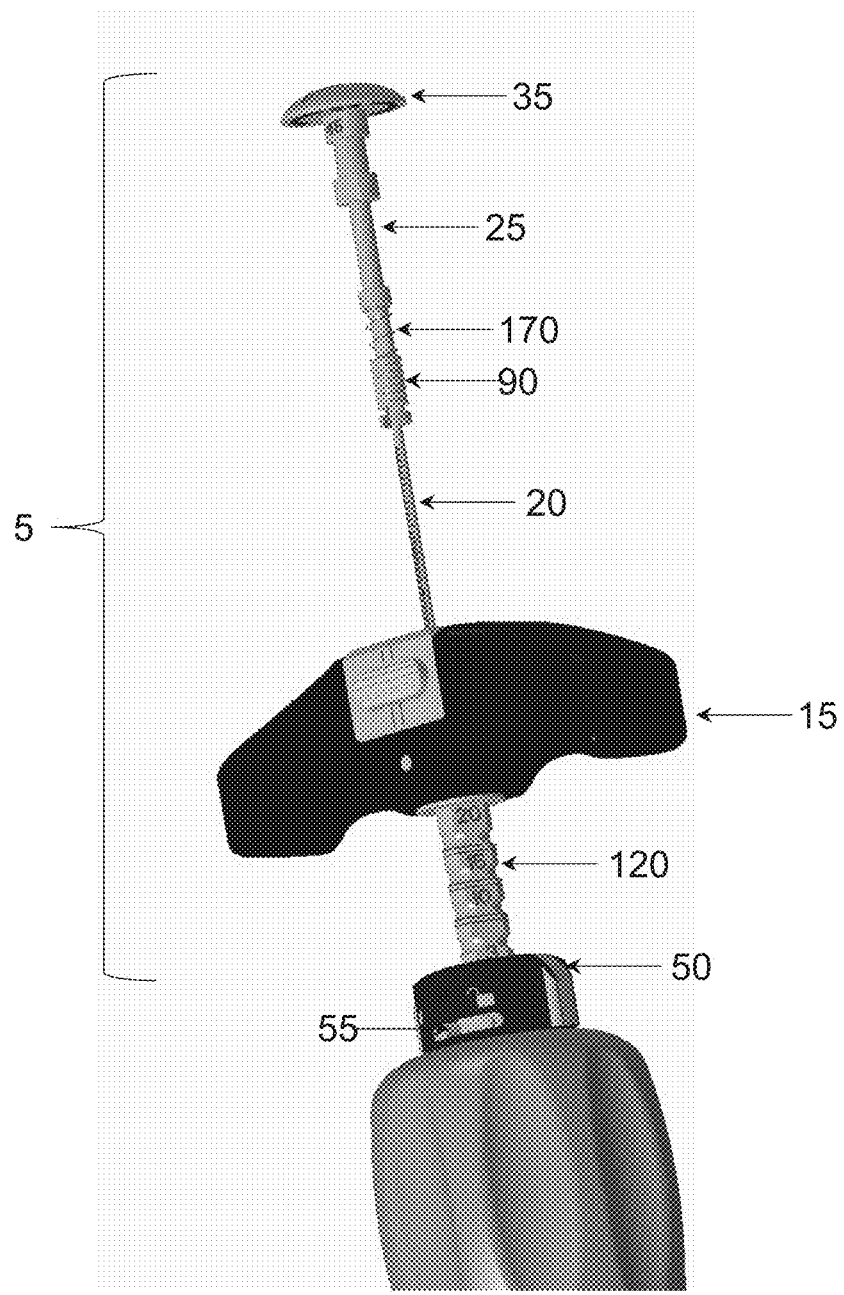
FIG. 4a is a closeup perspective view of a proximal section of an example bone anchor insertion device.

In FIG. 4a, an embodiment of bone anchor insertion device (105) is shown. In this embodiment, stylet (20) and shuttle (25) are engaged and their assembly is partially disengaged from the proximal section (5) to illustrate the way the components mate together. Locking collar (55) is in the unlocked position. Impaction cap (35) disposed on proximal end of shuttle (25) and engaged stylet (20) are shown in partially inserted position into proximal end of T-handle (15), with a portion of depth indicator (120) at distal end of T-handle (15) shown to illustrate gradation marking for various depths that surgeon may choose in operating bone anchor insertion device (105). Shuttle spring (170) and threads (90) on distal portion of shuttle are also shown, with threads (90) covering proximal end of stylet (20). Collar (50) surrounding distal portion of depth indicator (120) and locking collar (55) residing on proximal portion of axial handle (75) are also shown. Locking collar (55) is shown in the unlocked position, which allows depth indicator (120) to translate in a proximal or distal direction.

Figure 4B:
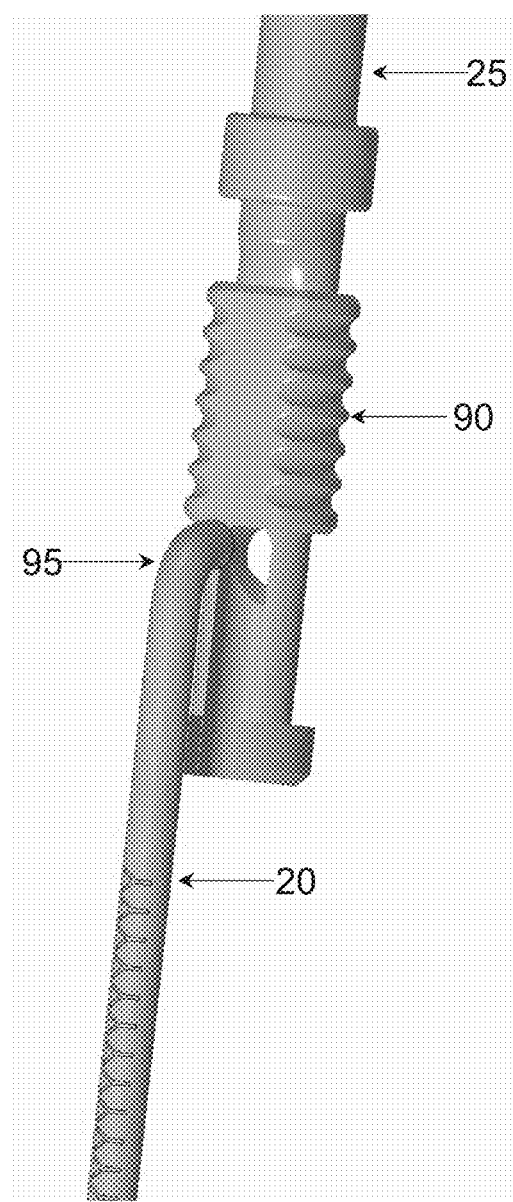
FIG. 4b is a closeup perspective view of an example J-bend of a stylet proximal end and a corresponding shuttle mating portion.

In FIG. 4b, an embodiment of bone anchor insertion device (105) is shown. This closeup view provides enhanced detail of an embodiment in which shuttle (25) distal portion interfaces with the proximate end of stylet (20). In particular, J-bend (95) mates with a receiving portion on the distal end of shuttle (25). Shuttle cuff (30—not shown) is pulled back to allow stylet (20) to enter the mating channel of the shuttle (25). Threads (90) are shown in cutaway view and shuttle sleeve (not shown) can translate distally to further house mated J-bend (95) of stylet (20). The shuttle cuff (30—not shown) is pulled back to allow the stylet (20) to enter the mating channel of the shuttle (25). This image illustrates one method of assembly of this embodiment of the stylet (20) and shuttle (25). Other methods of engaging the stylet (20) and the shuttle (25) may be employed.

Figure 4C:
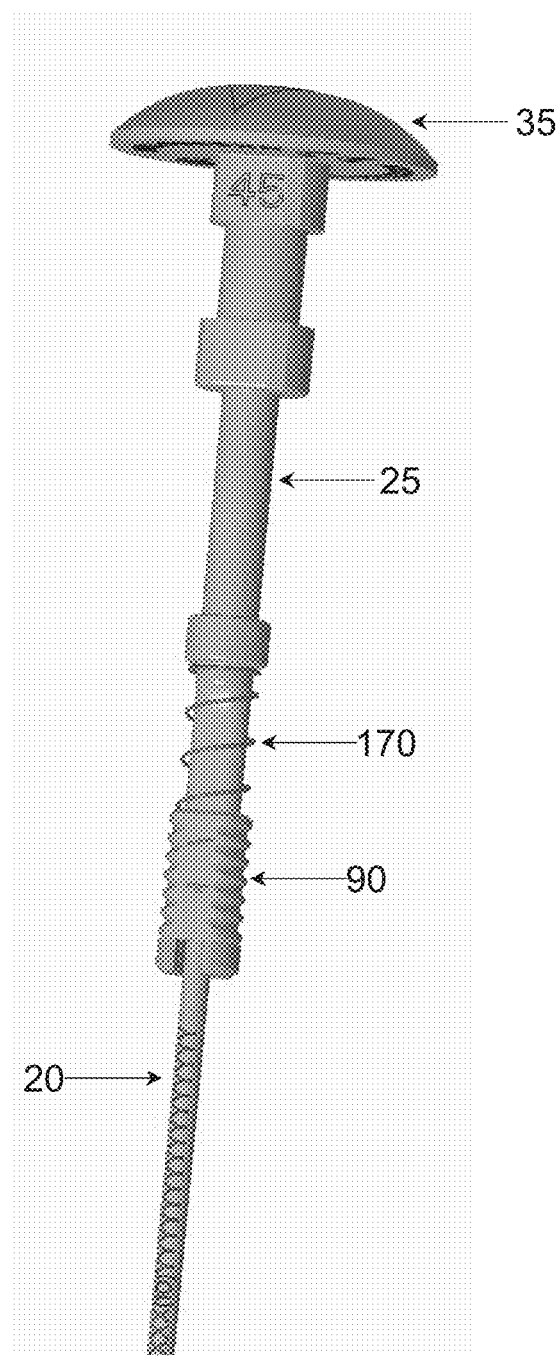
FIG. 4c is a perspective view showing the proximal end of an assembled shuttle, stylet, impaction cap, shuttle spring and shuttle cuff of an example bone anchor insertion device.

In FIG. 4c, an embodiment of bone anchor insertion device (105) illustrates a removable assembly of impaction cap (35), which is disposed on proximal end of shuttle (25), stylet (20) engaged by distal end of shuttle (25), and stylet tip (70—not shown) at distal end of stylet (20). Shuttle spring (85) and threads (90) are located on distal portion of shuttle. The image focuses on the shuttle (25) to provide additional detail. The shuttle cuff (30) covers the portion of the stylet (20) that mates with the shuttle (25) to prevent disengagement. The shuttle spring (170) applies a force to the shuttle cuff (30) to prevent it from unintentionally backing up and allowing the stylet (20) to be released. In particular, impaction cap (35), shuttle (25), and a proximal portion of stylet (20) are illustrated in a magnified view. This image illustrates an assembled stylet (20) and shuttle (25) of this embodiment.

Figure 4D:
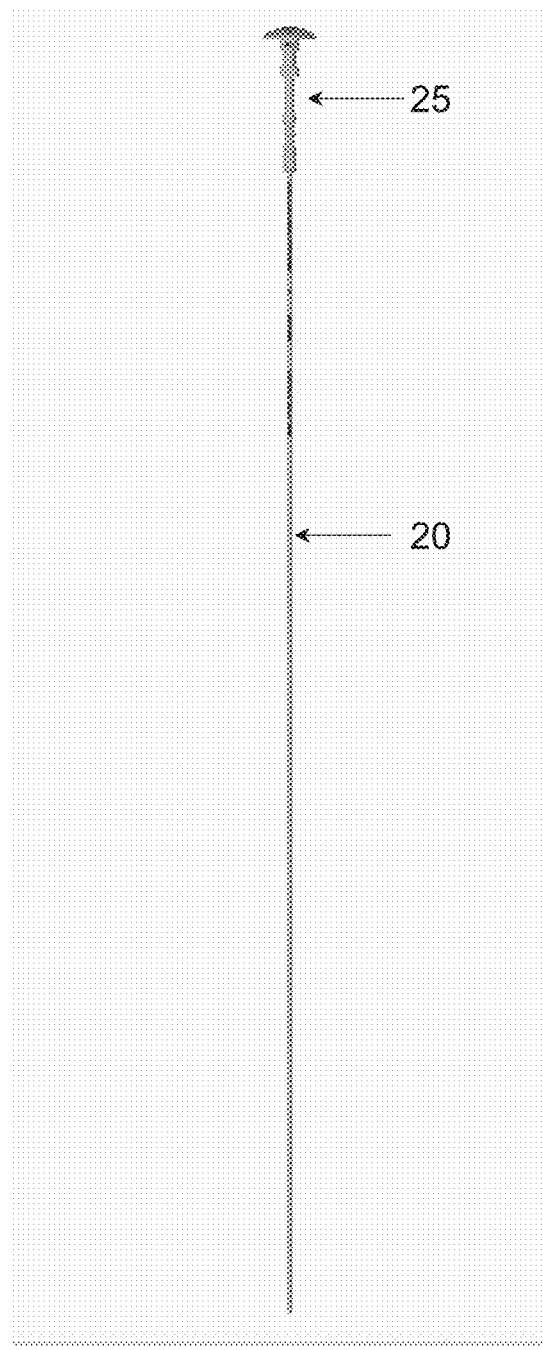
FIG. 4d is a view of an assembled shuttle, stylet and impaction cap of an example bone anchor insertion device.

In FIG. 4d, an embodiment of the fully assembled stylet (20) and shuttle (25) is shown. This image displays the full stylet (20) and shuttle (25) to communicate length and scale, although various lengths of stylet (20) and shuttle (25) are acceptable and usable with this embodiment.

Figure 5:
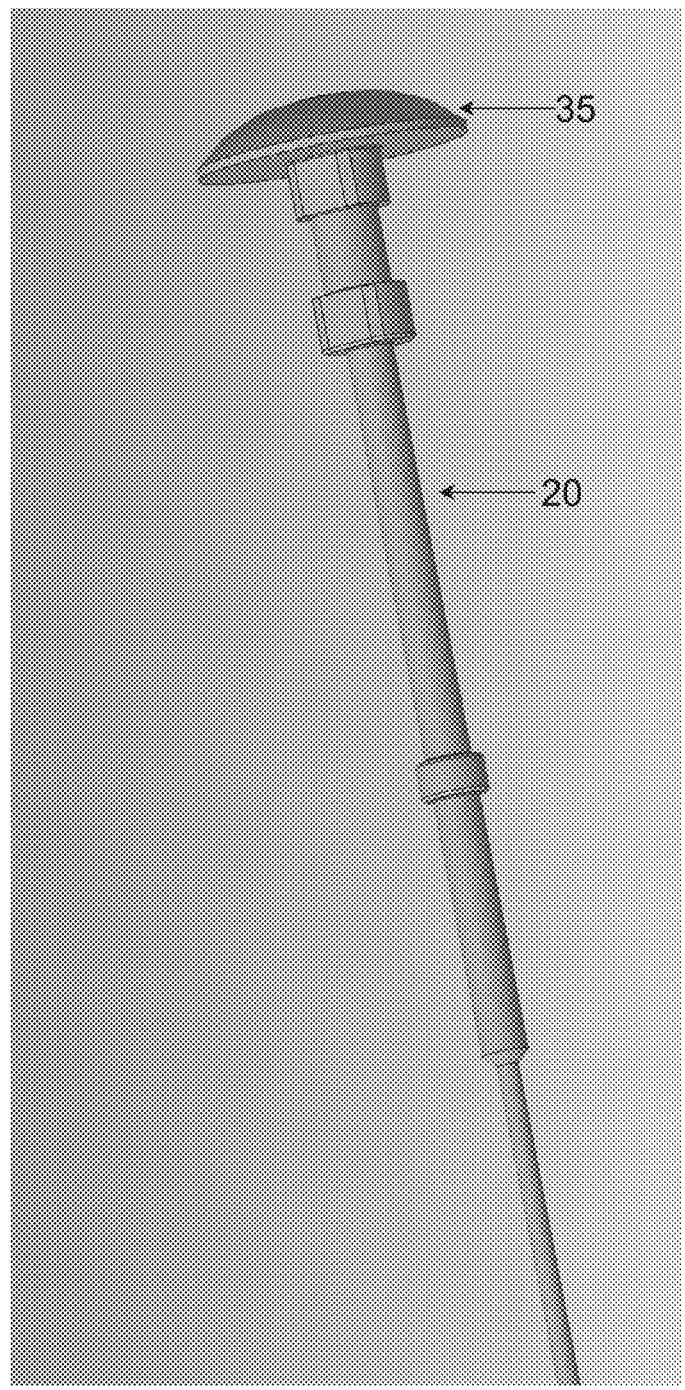
FIG. 5 is a perspective view of the proximal end of an assembled stylet, shuttle and impaction cap of an example bone anchor insertion device.

In FIG. 5, an embodiment of bone anchor insertion device (105) is shown. In this embodiment, stylet (20) contains features to engage directly with proximal section (5) and is disassembled from bone anchor insertion device (105) for ease of reference. In this embodiment, no separate shuttle is employed. In particular, impaction cap (35) is illustrated in a magnified view.

Figure 6A:
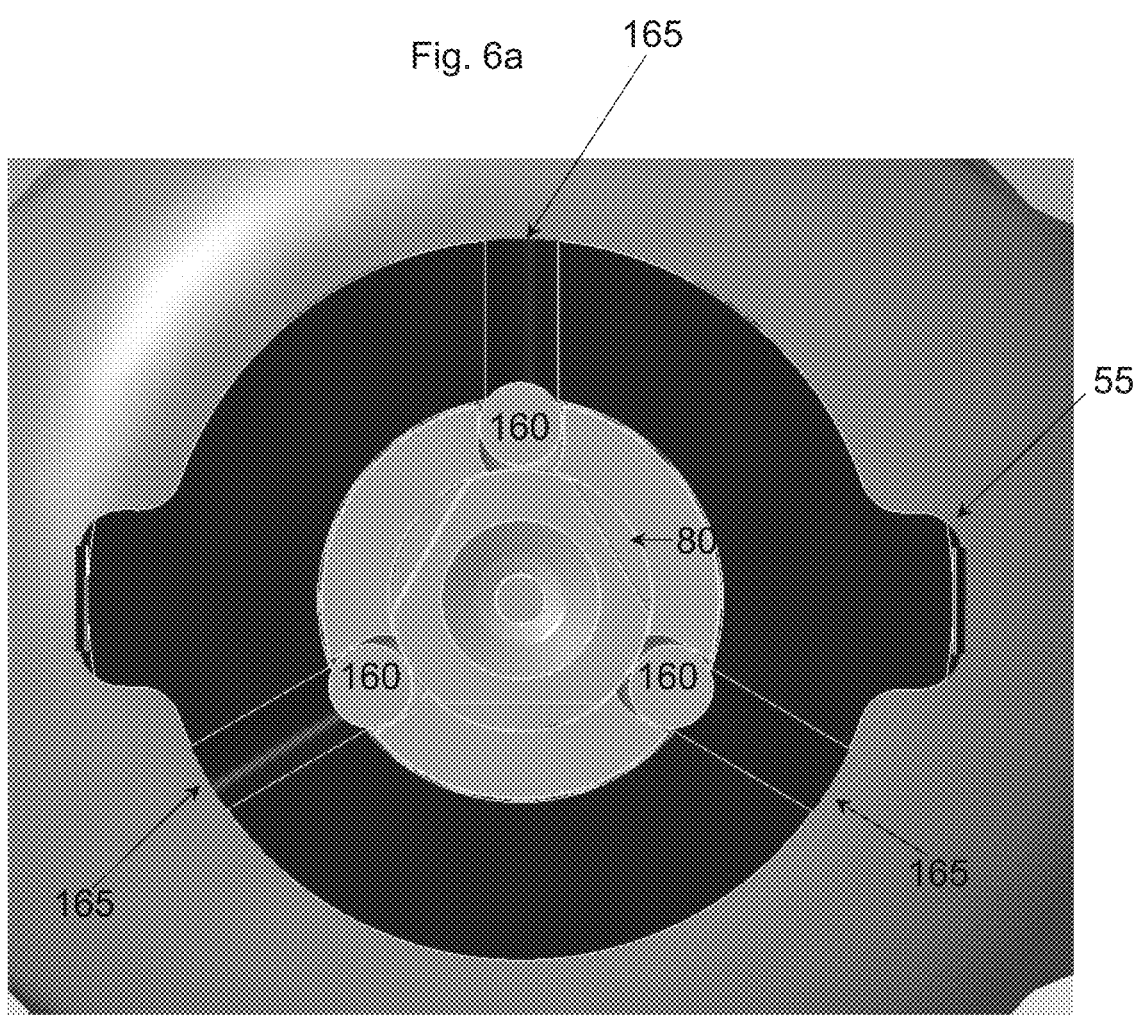
FIG. 6a is an internal view of a lock in the engaged (locked) position of an example bone anchor insertion device.

In FIG. 6a, an embodiment of bone anchor insertion device (105) is shown. In this embodiment, locking collar (55) is shown in the unlocked position from an internal top view. In this embodiment, balls (160) are aligned with channels (165). The channels (165) allow the balls (160) to avoid obstructing translation of the proximal section shaft (80), thus allowing the shaft (80) in proximal section (5) to translate.

Figure 6B:
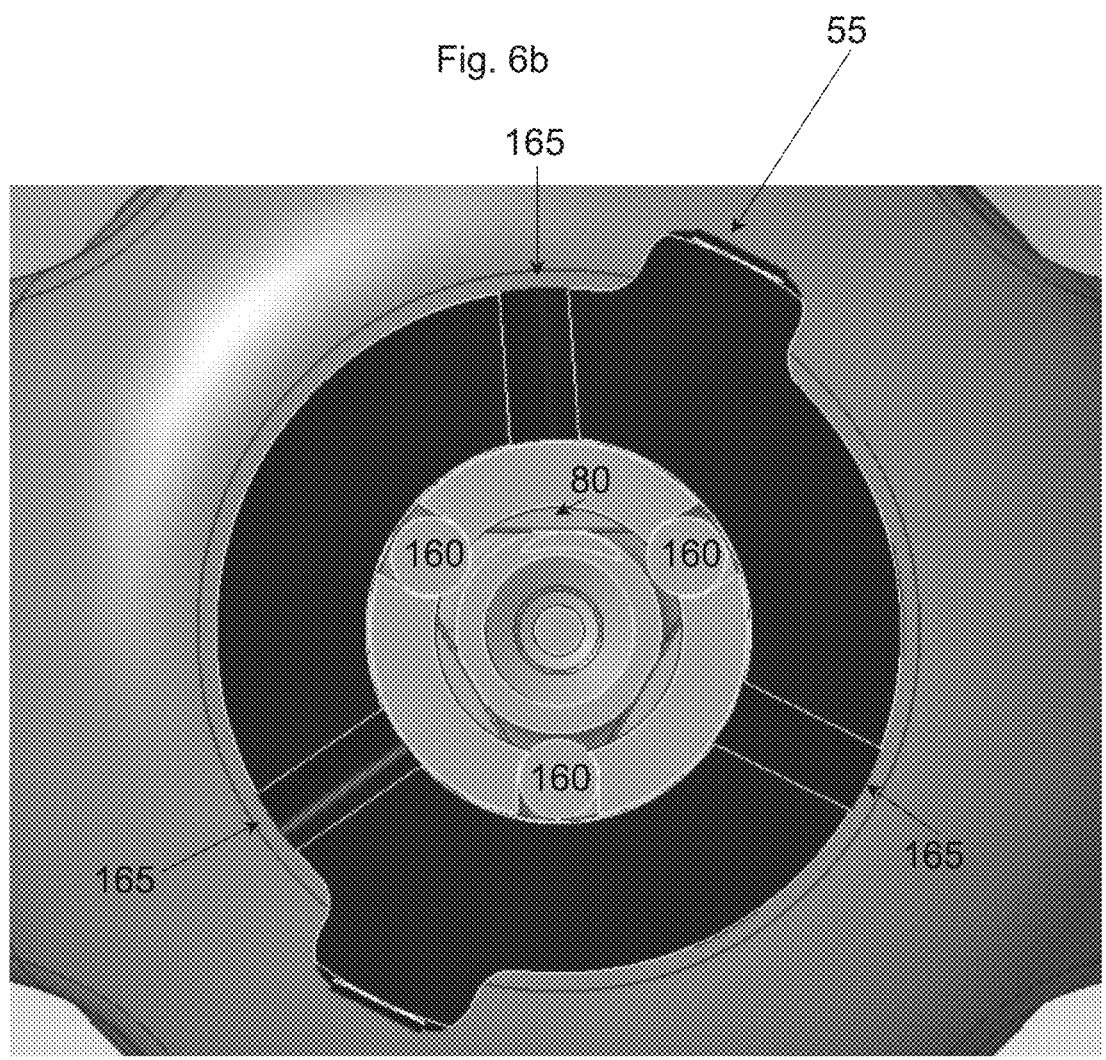
FIG. 6b is an internal view of a lock in the disengaged (unlocked) position of an example bone anchor insertion device.

In FIG. 6b, an embodiment of bone anchor insertion device (105) is shown. In this embodiment, locking collar (55) is shown in the locked position from an internal top view. In this embodiment, the balls (160) are not aligned with the channels (165), so the wall of the collar (50) forces the balls (160) into the grooves formed in the shaft (80) of the proximal section (5). When the balls (160) are forced into the grooves, the path of the major diameter of the proximal section shaft (80) is blocked and the ability of it to translate is obstructed.

Figure 6C:
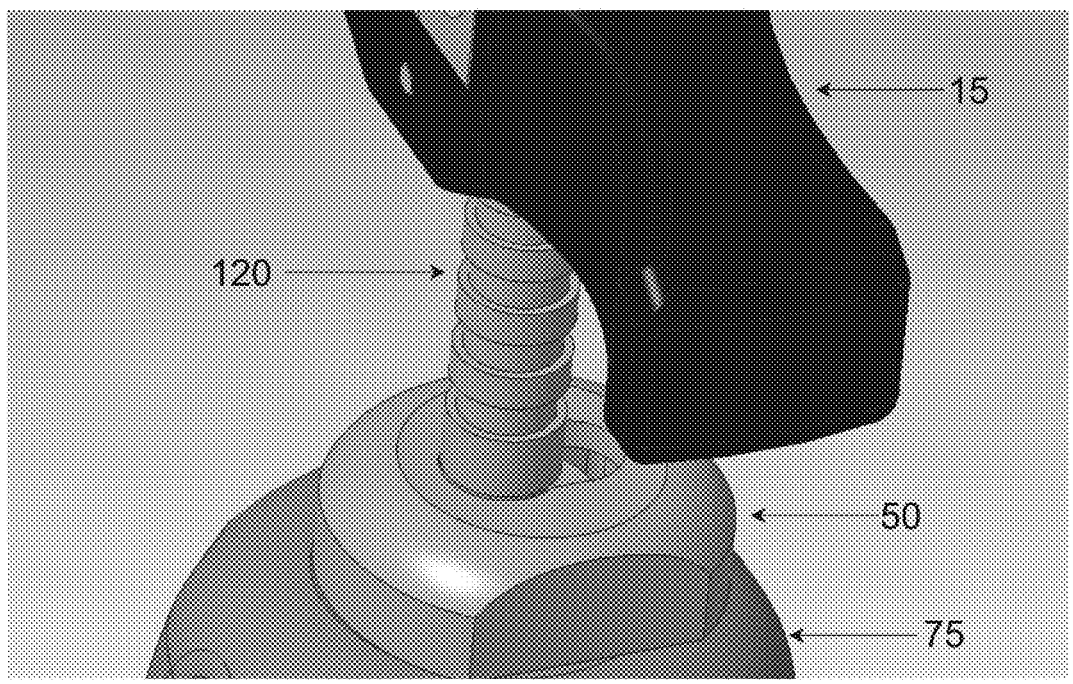
FIG. 6c is a perspective view of a T-handle and depth indicator of an example bone anchor insertion device.

In FIG. 6c, an embodiment of bone anchor insertion device (105) is shown. In particular, a magnified view of T-handle (15), depth indicator (120), collar (50), and axial handle (75) are shown. In this embodiment, the locking collar (55) is horizontally translatable and has two connected holes of different sizes. In the image shown, the collar (50) is in the unlocked position and the larger hole is aligned with the depth indicator (120), allowing translation.

Figure 6D:
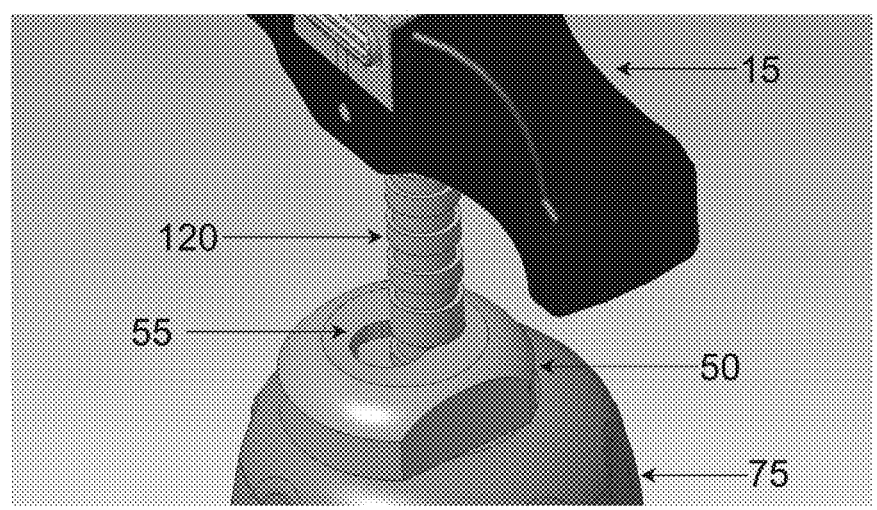
FIG. 6d is a perspective view of a T-handle in an unlocked position of an example bone anchor insertion device.

In FIG. 6d, an embodiment of bone anchor insertion device (105) is shown. In particular, a magnified view of T-handle (15), depth indicator (120), collar (50), and axial handle (75) are shown. In this embodiment, the locking collar (55) is horizontally translatable and has two connected holes of different sizes. As shown in this embodiment, the collar (50) is in the locked position and the smaller hole is aligned with the depth indicator (120). The lip of the smaller hole is engaged with a groove on the depth indicator (120), obstructing translation.

Figure 7A:
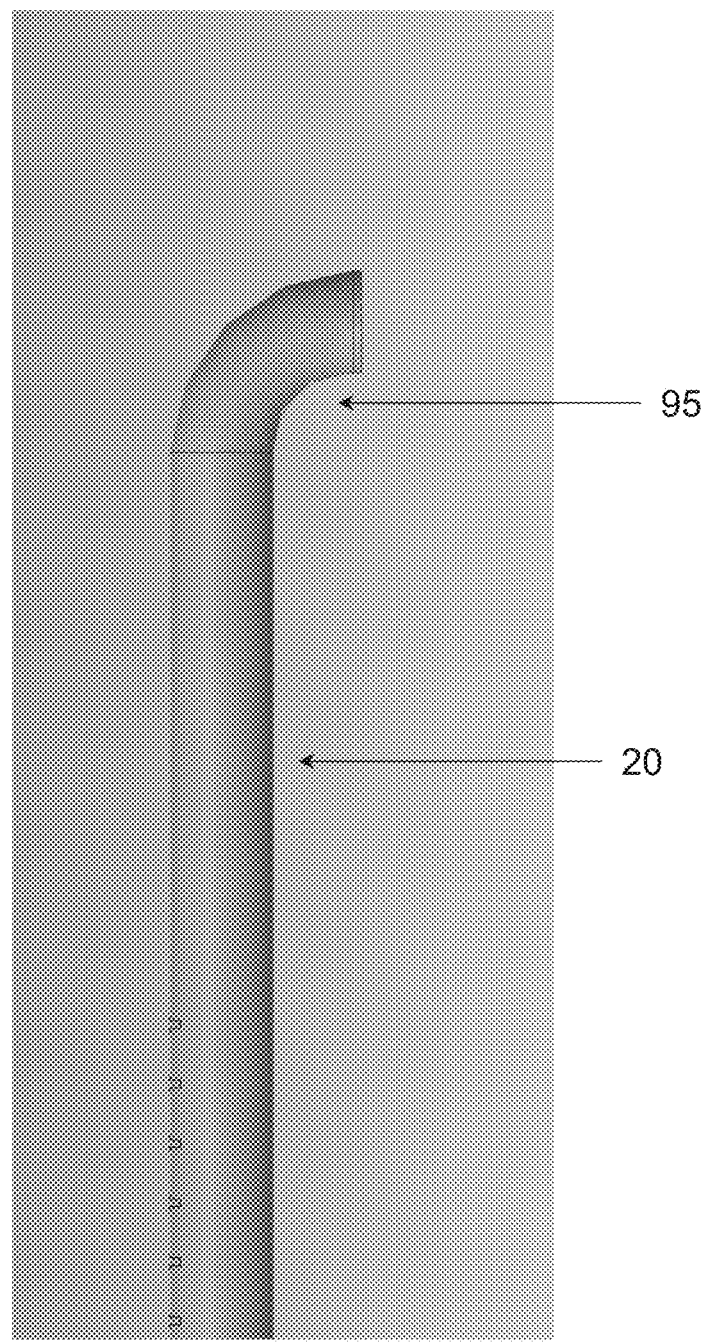
FIG. 7a is a closeup view of a stylet with a J-bend in the proximal end of an example bone anchor insertion device.

In FIG. 7a, an embodiment of stylet (20) of bone anchor insertion device is shown. In this illustrated embodiment, the proximal end of stylet (20) has a J-bend (95) configuration. As shown and described here and in relation to FIG. 4c, J-bend (95) of stylet (20) mates to a corresponding receiving portion of shuttle (25), and is optionally engaged with shuttle cuff (30) to further secure stylet (20) in a desired position.

Figure 7B:
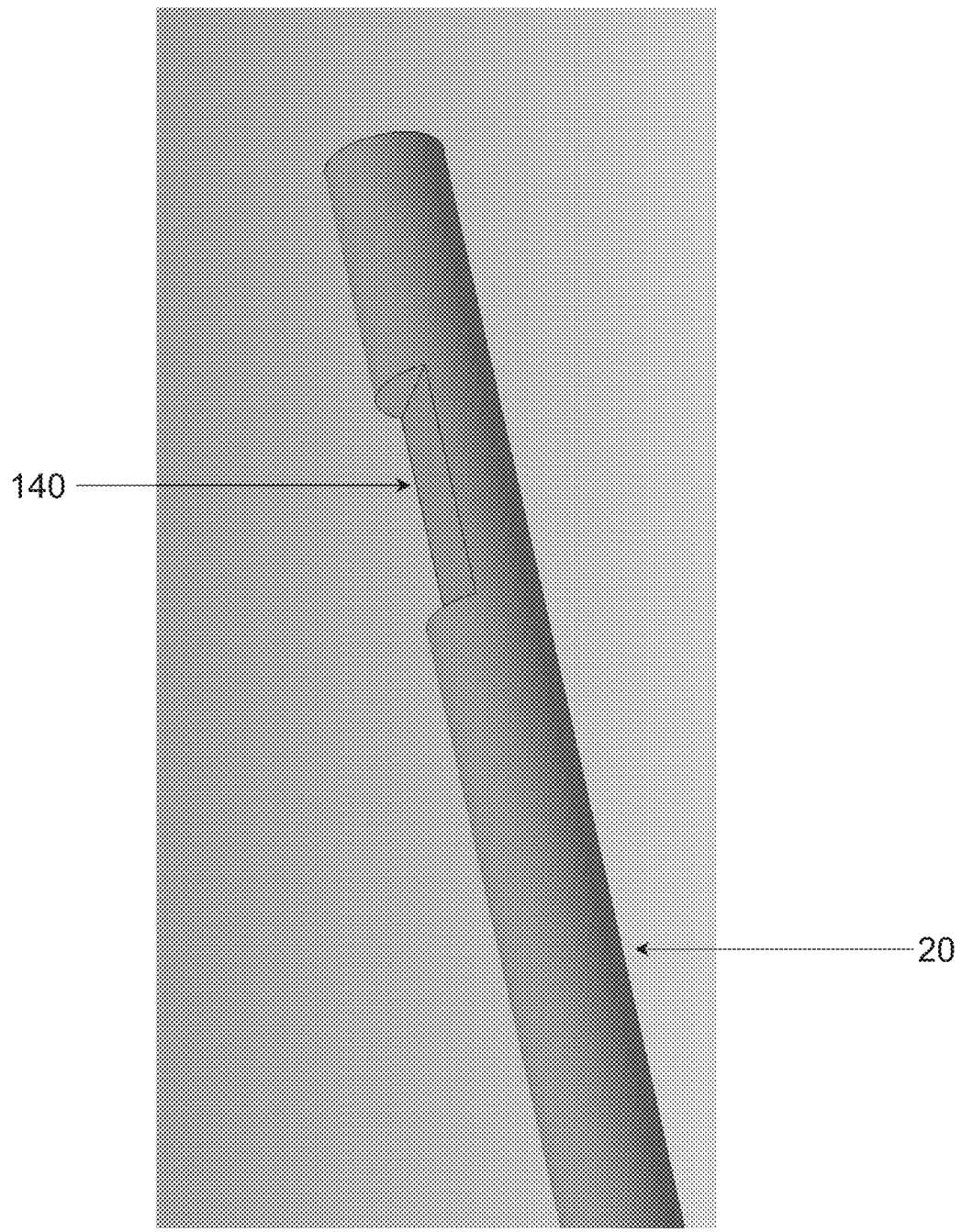
FIG. 7b a closeup perspective view of a stylet with an alternative cutout in the proximal portion of an example bone anchor insertion device.

In FIG. 7b, an embodiment of stylet (20) of bone anchor insertion device is shown. In this illustrated embodiment, the proximal end of stylet (20) has a cutout (140) configuration. As shown and described here, cutout (140) of stylet (20) mates to a corresponding receiving raised portion of shuttle (25), and is optionally engaged with shuttle cuff (30) to further secure stylet (20) in a desired position. In a related embodiment (not shown), cutout portion may reside on shuttle and raised portion may reside in corresponding proximal end of stylet (20) in order to mate and secure stylet (20) to shuttle (25). A shuttle cuff (not shown) optionally may also engage proximal portion of stylet (20) to further secure stylet (20) to shuttle (25).

Figure 7C:
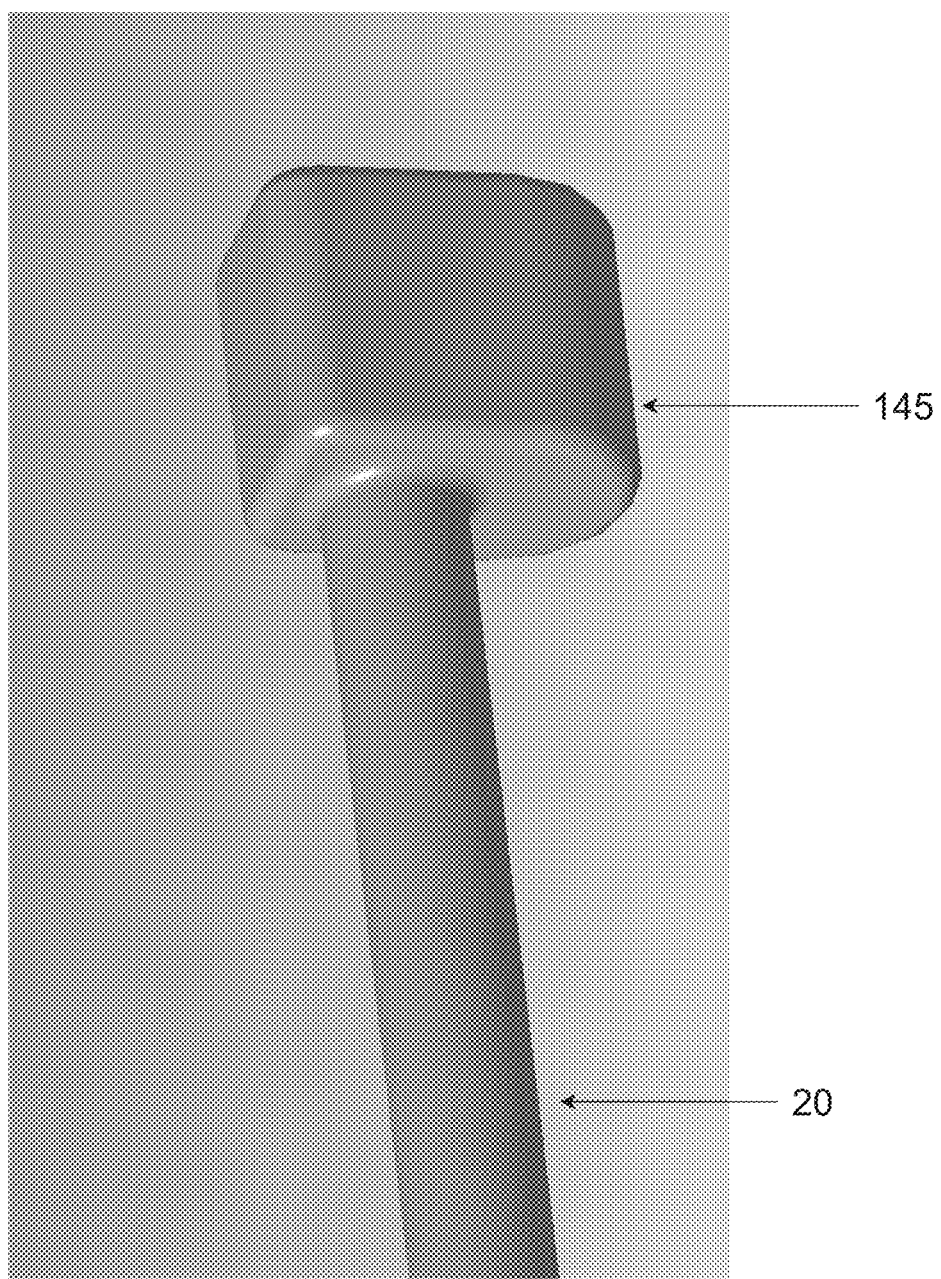
FIG. 7c is a closeup perspective view of a stylet with an alternative elliptical configuration in the proximal end of an example bone anchor insertion device.

In FIG. 7c, an embodiment of stylet (20) of bone anchor insertion device is shown. In this illustrated embodiment, the proximal end of stylet (20) has an elliptical end (145) configuration. As shown and described here, elliptical end (145) of stylet (20) mates to a corresponding receiving portion of shuttle (25), and is optionally engaged with shuttle cuff (30) to further secure stylet (20) in a desired position. A shuttle cuff (not shown) optionally may also engage proximal portion of stylet (20) to further secure stylet (20) to shuttle (25).

Figure 7D:
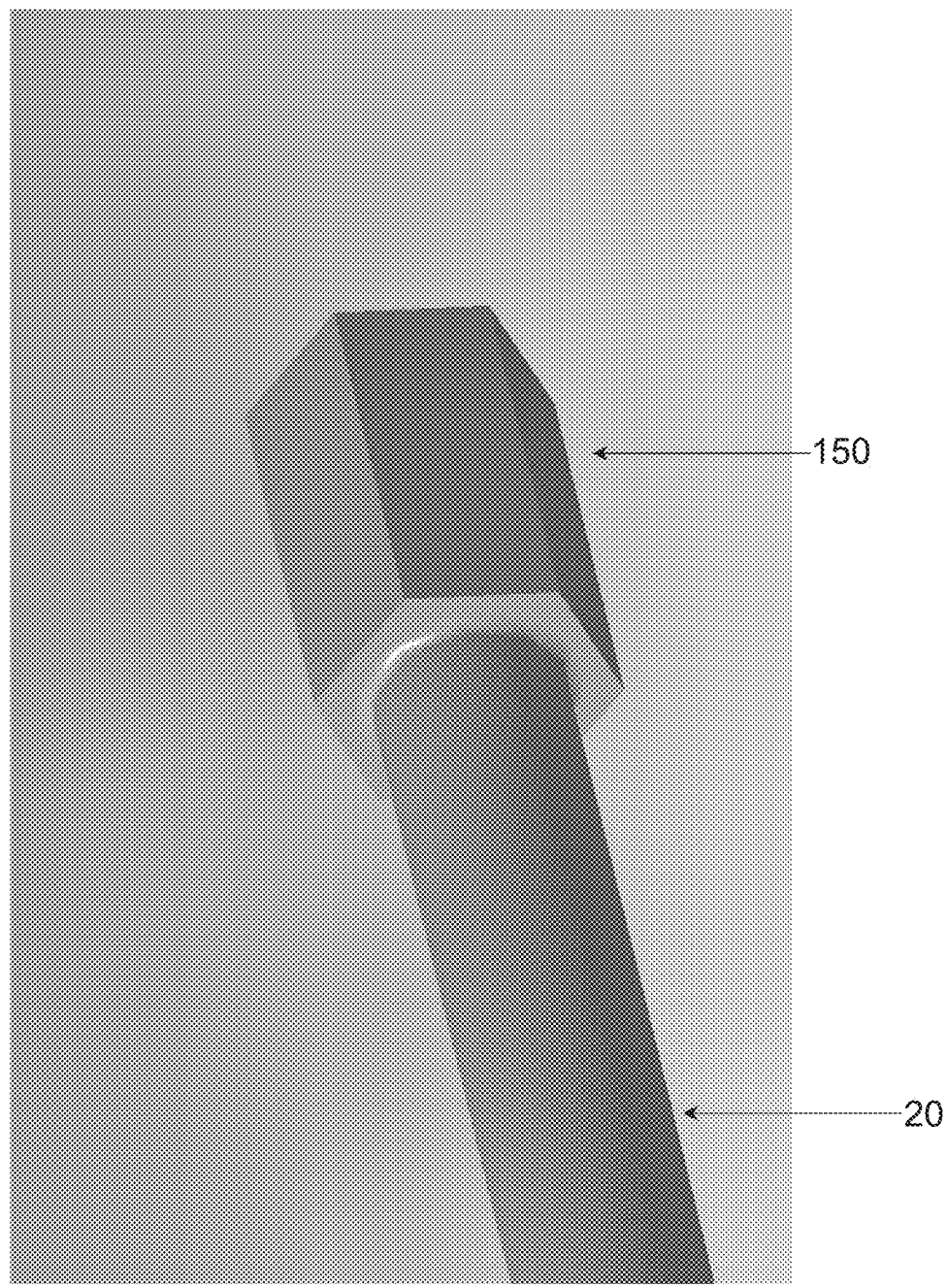
FIG. 7d is a closeup perspective view of a stylet with an alternative hexagonal configuration in the proximal end of an example bone anchor insertion device.

In FIG. 7d, an embodiment of stylet (20) of bone anchor insertion device is shown. In this illustrated embodiment, the proximal end of stylet (20) has a hexagonal end (150) configuration. As shown and described here, hexagonal end (150) of stylet (20) mates to a corresponding receiving recessed portion of shuttle (25), and is optionally engaged with shuttle cuff (30) to further secure stylet (20) in a desired position. A shuttle cuff (not shown) optionally may also engage proximal portion of stylet (20) to further secure stylet (20) to shuttle (25).

Figure 8B:
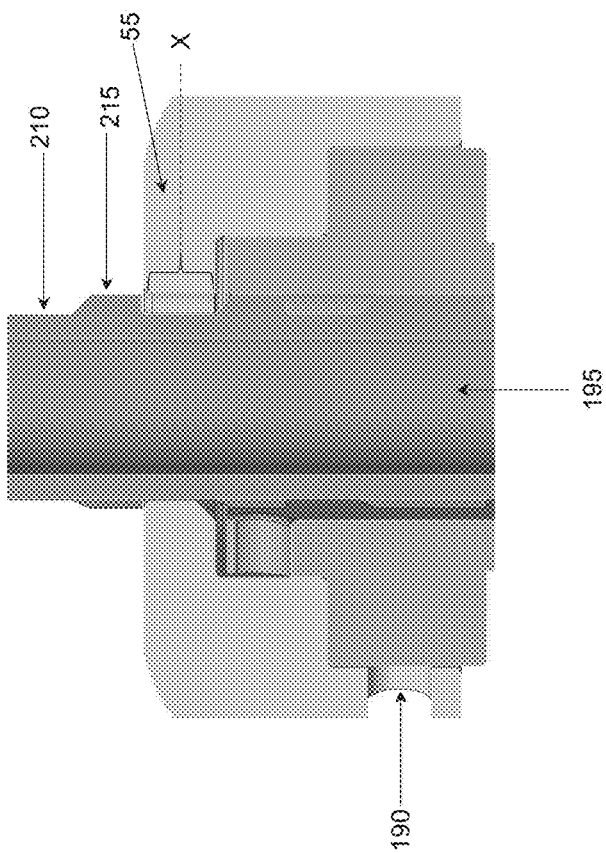
FIG. 8b is a cutaway side view of a proximal section of an example bone anchor insertion device illustrating a twist collar in an unlocked position.
Figure 8A:
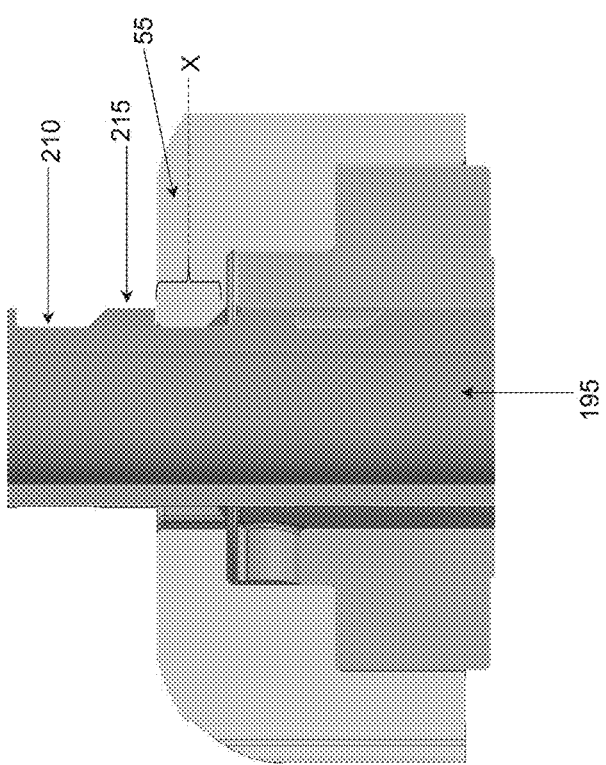
FIG. 8a is a cutaway side view of a proximal section of an example bone anchor insertion device illustrating a twist collar in a locked position.

In FIG. 8a, a cutaway side view of a proximal section of an example bone anchor insertion device illustrating a twist collar embodiment in a locked position is shown. In this illustrated embodiment, piston (195) is shown having at least one groove (210) and at least one node (215). This embodiment also illustrates that at least one node (215) is in a buttressing configuration. Further, position (X) illustrates the twist lock embodiment is in the engaged (locked) position, with locking collar (55) residing in groove (210) and bordered by node (215), so that piston (195) cannot axially translate.

In FIG. 8b, a cutaway side view of a proximal section of an example bone anchor insertion device illustrating a twist collar embodiment in an unlocked position is shown. In this illustrated embodiment, piston (195) is shown having at least one groove (210) and at least one node (215). This embodiment also illustrates that at least one node (215) is in a buttressing configuration. Further, position (X) illustrates the twist lock embodiment is in the disengaged (unlocked) position, with locking collar (55) not residing in groove (210), so that piston (195) can axially translate. Alignment screw port (190) is also shown in this embodiment.

In FIG. 9, a closeup perspective view of a proximal section of an example bone anchor insertion device illustrating a sliding collar in a disengaged (unlocked) position is shown. In this illustrated embodiment, depth indicators (120) are visible on one surface of piston (195). Sliding collar (50) is also shown along with locking collar (55), at least one node (215), and at least one groove (210). Alignment screw port (190) is also shown in this embodiment.

In FIG. 10a, a closeup view of an embodiment having a sliding collar lock in the engaged (locked) position of an example bone anchor insertion device is shown. In this illustrated embodiment, sliding collar (55) is shown residing in groove (210) of piston (195) and engaged with node (215) so that piston (195) does not translate. Alignment screw (185) is also illustrated.

In FIG. 10b, a closeup view of an embodiment having a sliding collar lock in the disengaged (unlocked) position of an example bone anchor insertion device is shown. In this illustrated embodiment, sliding collar (55) is shown disengaged from groove (210) of piston (195) and correspondingly disengaged from node (215) so that piston (195) may translate. Alignment screw (185) is also illustrated.

In FIG. 11a, a top view of an embodiment of a collar lock in the disengaged (unlocked) position of an example bone anchor insertion device is shown. In this illustrated embodiment, collar (55) having at least one stopper (180) or a plurality of stoppers (180) and at least one lobe (175) or a plurality of lobes (175) allows rotation of piston (195).

In FIG. 11b, a top view of an embodiment of a lock in the engaged (locked) position of an example bone anchor insertion device is shown. In this illustrated embodiment, collar (55) having at least one stopper (180) or a plurality of stoppers (180) and at least one lobe (175) or a plurality of lobes (175) does not allow rotation of piston (195) when lobe (175) is engaged with stopper (180).

In FIG. 12a, a cutaway side view of a collar lock in the engaged (locked) position of an example bone anchor insertion device is shown. In this illustrated embodiment, lobe (175) is engaged with groove (210) to lock vertical translation of piston (195). Window (200) provides visual confirmation of lock status in this embodiment, such that the user may determine if piston is in the locked or unlocked state. Ball detent (205) may allow a user to apply a force to move the lock from one position to another (e.g., from a locked to unlocked position, or from an unlocked to a locked position).

In FIG. 12b, a cutaway side view of a collar lock in the disengaged (unlocked) position of an example bone anchor insertion device is shown. In this illustrated embodiment, lobe (175) is disengaged from groove (210) to allow vertical translation of piston (195).

In one or more embodiments, stylet is held rigid and immovable relative to the proximal section of the bone anchor insertion device. For example, the stylet in such embodiments does not rotate or translate relative to the proximal section of the bone anchor insertion device.

In one or more embodiments, the stylet directly interfaces with the proximal section of the bone anchor insertion device. In other embodiments, the stylet optionally indirectly interfaces with the proximal section of the bone anchor insertion device.

In one or more other embodiments, a shuttle is an optional intermediary component that mates rigidly and immovably with both the stylet and proximal section of the bone anchor insertion device, so that the stylet may be controlled, for example, via operation of the proximal section. The shuttle may mate with the stylet in various ways. In one or more embodiments, a bend in the stylet locks into a corresponding recess in the shuttle. In other embodiments, the stylet mates with the shuttle in more than one rotational orientation.

In one or more embodiments, a bone anchor insertion devices includes a retractable stylet, facilitating varying emergence lengths of the stylet from the bone anchor shank at the distal tip of the bone anchor insertion device.

Various stylet tip options are included in one or more embodiments of the bone anchor insertion device. One or more of the stylet tip options may also employ a cannula. For example, one embodiment employs a trocar stylet tip.

Another stylet example employs a beveled tip, which facilitates changes in trajectory once already inside the bone. During a surgical procedure, the surgeon can orient the beveled tip to impact bone in a directional manner, then rotate the tip to adjust the direction of the tip as the tip is driven further into the bone. In this embodiment, the stylet is rotationally controlled either directly to the proximal section or to the shuttle, which in turn is rotationally controlled to the proximal section. In these embodiments, the stylet cannot rotate relative to the proximal section, so rotating the proximal section changes the orientation of the sharp tip of the bevel. In this embodiment, a visual indicator communicates the direction of the sharp tip of the bevel, allowing trajectory in the bone to be modified. The beveled stylet tip angle ranges from about 15 to about 75 degrees.

A further example employs a diamond stylet tip. Other stylet tip configurations may be employed with the bone anchor insertion device, and the above examples are not intended to limit this or any other feature of the bone anchor insertion device.

In one or more embodiments, the handle spring applies a force to the proximal section. The handle spring allows the stylet to sit in the most retracted position when no force is applied to the proximal section. When the stylet is extended in bone, the force applied by the handle spring aids in retraction of the stylet such that the bone anchor screw will advance over the stylet with minimal forward movement of the tip of the stylet. In one or more embodiments, the stylet includes design features to facilitate tip orientation and control. In one example, a proximal portion of the stylet includes a hook-like feature that engages with a female mating feature in the shuttle or proximal section of the bone anchor insertion device. In another example, a cutout female feature on the proximal portion of the stylet engages with a corresponding male feature on the shuttle that holds the stylet.

A further example employs an enlarged asymmetric/directional feature that mates with the shuttle or proximal portion in one position (for a directional stylet tip) or up to 12 positions (for a non-directional stylet tip). Still another example provides a shuttle or proximal portion that applies a clamping force to the stylet to prevent rotation and translation.

In one or more embodiments, a collar may be located on the distal section of the bone anchor insertion device. The collar itself may also include a lock to secure it onto a specific position on the bone anchor insertion device. In an embodiment, the collar is a component of the lock, providing the user interface of the lock and integrating with other components to allow or prevent translation of the proximal section. In this embodiment, the user manipulates the collar to lock and unlock translation of the proximal section. The collar also helps the lock engage, though it does not directly interact with the piston. The collar contains recesses that the balls sit in, removing obstruction from the path of the piston and allowing translation. When the collar is manipulated such that the recesses no longer align with the balls, the walls of the collar force the balls to sit partially in the grooves cut into the piston, obstructing translation.

In an embodiment, the collar functions to engage or disengage the lock, wherein the lock is generally located on the distal section of the bone anchor insertion device. When the collar engages the lock, the proximal portion may not axially translate relative to the distal portion of the bone anchor insertion device. The collar engages the lock by applying, for example, axial, radial or rotational force to the collar. In one embodiment, the collar engages the lock by pushing/pulling the collar along the central axis. In another embodiment, the collar engages the lock via pushing the collar generally perpendicular to the axis of translation to secure the translating portion in a channel that prevents movement. In another embodiment, the collar engages the lock via squeezing one or multiple side sections of the collar in toward the central axis, such that the squeezed sections are cut-in springs or separate pieces that can flex, move, or pivot toward and away from the central axis to engage and disengage the lock.

In one or more other embodiments, a user engages the locking collar via rotating the collar about the central axis of the device.

Several optional configurations may be employed for preventing axial translation. In one or more embodiments, a bone anchor insertion device has a plurality of objects such as small balls that are forced to protrude into mating recesses, thereby blocking translational movement. In another example, a bone anchor insertion device frictionally prevents or minimizes translation by applying a gripping force to the shaft of the bone anchor insertion device. A further example provides engaging a lip with a mating shelf or recess to minimize or block translation. Still another example provides engaging a series of interfacing teeth formed from multiple lips and shelves/recesses to minimize or block translation.

In one or more embodiments, when the lock is in the disengaged position, the proximal section may freely translate in the axial direction. In one example, the proximal portion translates with resistance in the axial direction due to force applied to the shuttle or proximal section by a unidirectional spring in the bone anchor insertion device. In another example, the proximal section translates with resistance in the axial direction due to tension applied to the shuttle or proximal section by an elastically deforming band. In a further example, the proximal section translates with resistance in an axial direction due to changes in air or fluid pressure in a portion of the bone anchor insertion device.

In one or more embodiments, ratcheting mechanism is located on distal portion of the handle. The term "ratcheting mechanism" and "ratchet" are used interchangeably throughout this disclosure. The ratchet allows a user to apply rotational force in a singular direction without transmitting rotational force in the corresponding opposite direction when operating the bone anchor insertion device. In one or more embodiments, the ratchet is operated by applying rotational force only in the clockwise direction. In other embodiments, a user operates the ratchet by applying rotational force only in the counter-clockwise direction. In one or more other embodiments, the handle is lockably engaged with the shaft so that rotational force applied by the user directly translates to rotational motion corresponding to the direction (e.g., clockwise or counter-clockwise) in which the force was applied.

In one or more embodiments, handle has a quick-connect feature whereby the bone anchor insertion device handle mates to a shaft with a corresponding male attachment. Thus, one handle may be used with multiple driver configurations, including, for example, standard MIS, navigation MIS, and shank-only drivers. The term "MIS" denotes minimally invasive surgery.

In one or more embodiments, the bone anchor insertion device accommodates varying lengths of drivers that range from about 2 to about 20 inches in length. In other embodiments, the bone anchor insertion device accommodates varying lengths of stylets that range from about 4 to about 30 inches, as well as accommodating varying stylet tip options.

In one or more embodiments, the bone anchor insertion device employs multiple proximal section configurations to accommodate different anchor screw lengths and associated variable stylet positions. For example, a single shuttle having multiple seat configurations accommodates varying stylet positions, depending on the desired stylet position. In another example, one or more designated shuttles or proximal sections with a variety of designated stylet seats are employed for bone anchor screws having specific diameter and/or screw length dimensions. Multiple shuttle configurations and proximal sections with multiple seat configurations may also be employed to accommodate or customize varying stylet positions.

Components of the presently described anchor bone insertion device may be manufactured of various materials. Example materials include various metals and alloys thereof, including stainless steel, titanium, aluminum, and combinations thereof. Metals used in materials of construction for the bone anchor insertion device components also include nitinol (nickel titanium), and austenitic steels such as Nitronic 50 and Nitronic 60, for example. Silicone and silicone blends may also be used to fabricate one or more of the components in bone anchor insertion device. Further, materials of construction for one or more of the components of the present bone anchor insertion device include fluoropolymer and other plastics. Examples are: PEEK (polyetheretherketone); PPS (polyphenylene sulfide); PPSU (polyphenylsulfone); FEP (fluorinated ethylene propylene); PCTFE (polychlorotrifluoroethylene); PFA (perfluoroalkoxy); ETFE (ethylene tetrafluoroethylene); ECTFE (ethylene chlorotrifluoroethylene); combinations thereof, and the like.

In particular, materials of construction employed in one or more of the components in the bone anchor insertion device are able to withstand autoclaving, including parameters such as saturated steam under pressure (~1 atm), along with concomitant autoclave chamber temperatures ranging from about 100° C. to 150° C. for about 15 to 60 minutes.

In an exemplary embodiment demonstrating use of the bone anchor insertion device, a user such as a surgeon first accesses the target bone site, for example by creating an incision through tissue to expose the target bone site. The user then positions the distal tip of the bone anchor insertion device at the desired entry point on the target bone. In one or more embodiments, the distal tip can be the tip of the stylet or the tip of a shank. The user impacts the end of the proximal section to gain purchase into the target bone site. Impaction on the end of the proximal section causes the stylet to extend.

In an embodiment of the bone anchor insertion device in which a lock is present, the lock may be set in the unlocked position during the impaction step. In the event that a downward force is not being applied to the proximal section of the bone anchor insertion device, and if the lock is not engaged (i.e., the lock is in the unlocked position), then the stylet retracts as the shank moves over it into the bone.

The stylet may be actively retracted when in the unlocked position and as a force is applied to the proximal section of the bone anchor insertion device, such as by pushing the user's hand or a hammer against the proximal section, or some other similar method of applying force to the proximal section.

A user rotates the handle of the bone anchor insertion device to thread an attached bone anchor into the target bone site. The rotation may be full or partial, depending on the desired depth to drive the anchor. In one or more embodiments, the handle may also include a ratcheting mechanism. Rotation of the handle causes rotation of the entire bone anchor insertion device; the proximal and distal sections of the device do not move separately from each other.

If a user desires to completely remove the stylet from the target bone site, the user presses the relevant button (not shown) on the proximal section to release and apply force to the upper (proximal) portion of the shuttle. The release may be accomplished by applying force from a user's hand or from a slap hammer.

The disclosed bone anchor insertion device eliminates the need for guidewires, jamshidis, and/or related conventional pedicle access instrumentation utilized in percutaneous bone anchor assemblies. The streamlined process afforded through use of the bone anchor insertion device thus reduces the duration of surgical procedures, while simultaneously providing optimum intraoperative feedback and surgeon control.

In the bone anchor insertion device, the T-Handle includes a function of managing depth of the stylet, so that the surgeon has measured control over the depth in which to insert a bone anchor screw or related anchor device. The stylet depth can be controlled within a range of about 1 to 35 mm, including an example range of about 3 to 25 mm, and bone anchor screws of varying dimensions can be used with the bone anchor insertion device. For example, bone anchor screws having a length of about 15 to 80 mm can be used, including an example range of about 30 to 60 mm, with the bone anchor insertion device.

In one example, a shuttle is employed in the bone anchor insertion device. The shuttle length can vary, depending on the desired length of the bone screw or bone anchor device.

The bone anchor insertion device also provides various stylet tip configurations, including a beveled tip stylet, a diamond tip stylet, a navigation bevel tip stylet, a navigation diamond tip stylet, and the like. The bone anchor insertion device also includes further stylet tip configurations, which depend on the surgeon's preferred methodology and the desired surgical application. Stylets employed with the bone anchor insertion device may be replaceable, disposable, or reusable. A user may also choose to redirect the stylet as it enters into the target bone site, and/or as the stylet tip continues to travel deeper into the bone. For example, in one or more embodiments, a bevel stylet tip provides directionality due to the relevant angle of the tip, with the bevel pointing in the direction of the path of travel for the stylet tip as the bone anchor insertion device drives the stylet into the bone. Directionality of the stylet tip may also be indicated by one or more markings on the proximal end of the bone anchor insertion device. Alternatively, a user may employ a stylet tip configuration that provides other additional advantages, depending on the desired bone anchor insertion point and the preferred path of travel for the anchor device into the bone.

In one or more embodiments, a removable or replaceable stylet engages with the shuttle. The stylet may be removably locked to the shuttle via a mating configuration on the proximal end of the stylet. Example stylet mating configurations include a J-bend, a hexagonal proximal end of the stylet, a notched proximal portion of the stylet, a stylet having an elliptical proximal end, and the like. FIGS. 7a through 7d provide examples of stylet tips that are within the scope of the present invention, and other stylet tip configurations are also contemplated.

A corresponding receiving (female) structure on the shuttle engages in a mating relationship with the corresponding (male) stylet mating configuration. For example, a stylet having a J-bend on the stylet proximal end engages a receiving port in the shuttle. As the stylet and shuttle mate to restrict stylet rotational movement, a retractable shuttle cuff may also reside on the distal portion of the shuttle to facilitate locking of the stylet to the shuttle. A shuttle cuff is also optionally included in other exemplary stylets and corresponding shuttles. The shuttle cuff generally resides on the distal portion of the shuttle. The shuttle cuff is pulled toward the proximal portion to expose the shuttle female mating mechanism. As the stylet male mating configuration engages the corresponding female mating mechanism on the shuttle, the shuttle cuff is then allowed to return to the closed (locked) position to further secure the stylet in its mating with the shuttle.

The bone anchor insertion device is fully compatible with conventional MIS (minimally invasive surgery) tulips and MIS towers used in relevant surgical procedures.

The methods and devices disclosed herein can provide a number of advantages. For example, in some embodiments, the time to target and place the bone anchor assembly can be reduced, the radiation exposure to the patient and to the surgical staff can be reduced, and procedural steps such as needle placement, guidewire insertion and removal, and tapping can be eliminated. By way of further example, in some embodiments, inadvertent advancement of instrumentation can be eliminated by controlling the guide projection depth throughout the procedure, risk of removing a guidewire during removal of a needle or tap can be eliminated, and bending or kinking of a guidewire can be prevented.

One of ordinary skill in the art will readily understand that any ordering of method steps implied by the drawings or description herein is not to be construed as limiting or requiring the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

Any publications and patent applications mentioned in the specification are indicative of the level of those skilled in the art to which this invention pertains. All publications and patent applications are hereby incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims. The devices and methods disclosed herein can be used in minimally-invasive surgery and/or open surgery. While the devices and methods disclosed herein are generally described in the context of advancing a bone anchor into a pedicle, it will be appreciated that the methods and devices disclosed herein can be used with any human or animal bone, implant, non-living object, and the like. Also, it should be understood that numerous changes may be made within the spirit and scope of the inventive concepts described. Accordingly, it is intended that the invention should not be limited to the described embodiments, but that it have the full scope defined by the following claims.

The invention claimed is:

1. A bone anchor insertion device comprising:
   (a) a proximal section comprising an impact-receiving region and a depth indicator;
   (b) a distal section comprising a handle, wherein said distal section interfaces with said proximal section;
   (c) a driver, wherein said driver interfaces with said distal section; and
   (d) a stylet;
   wherein said stylet resides in a channel extending from said proximal section through said distal section and through said driver, said proximal section translates without rotation relative to said distal section, and said depth indicator indicates a length that said stylet extends beyond a distal tip of said driver.

2. A bone anchor insertion device according to claim 1, wherein said proximal section and said distal section are removably interconnected.

3. A bone anchor insertion device according to claim 1, wherein said driver removably engages a bone anchor assembly, a screw, a shank, a tulip, or a combination thereof.

4. A bone anchor insertion device according to claim 1, wherein said proximal section further comprises a lock to fix a protrusion distance of said stylet from the distal end of said driver.

5. A bone anchor insertion device according to claim 1, wherein said distal section further comprises a spring, piston, hydraulic component, an elastic component, a magnetic component, or any combination thereof.

6. A bone anchor insertion device according to claim 1, wherein said distal section further comprises a collar.

7. A bone anchor insertion device according to claim 1, wherein said handle further comprises a ratcheting mechanism.

8. A bone anchor insertion device comprising:
(a) a proximal section comprising an impact-receiving region and a depth indicator;
(b) a distal section comprising a handle, wherein said distal section interfaces with said proximal section;
(c) a driver, wherein said driver is removably interconnected to said distal section; and
(d) a retractable stylet;
wherein said stylet resides in a channel extending from said proximal section through said distal section and through said driver, said proximal section translates without rotation relative to said distal section, and said depth indicator indicates a length that said stylet extends beyond a distal tip of said driver.

9. A bone anchor insertion device according to claim 8, wherein said proximal section and said distal section are fixedly interconnected.

10. A bone anchor insertion device according to claim 8, wherein said proximal section and said distal section are removably interconnected.

11. A bone anchor insertion device according to claim 8, wherein said driver removably engages a bone anchor assembly, a screw, a shank, a tulip, or a combination thereof.

12. A bone anchor insertion device according to claim 8, wherein said distal section further comprises a spring, piston, hydraulic component, an elastic component, a magnetic component, or any combination thereof.

13. A bone anchor insertion device comprising:
(a) a proximal section comprising an impact-receiving region and a depth indicator;
(b) a distal section comprising a handle, wherein said distal section interfaces with said proximal section;
(c) a driver, wherein said driver interfaces with said distal section;
(d) a shuttle; and
(e) a stylet;
wherein said shuttle engages with said proximal section to control rotation and translation of said stylet, said proximal section translates without rotation relative to said distal section, and said depth indicator indicates a length that said stylet extends beyond a distal tip of said driver.

14. A bone anchor insertion device according to claim 13, wherein said proximal section and said distal section are fixedly interconnected.

15. A bone anchor insertion device according to claim 13, wherein said proximal section and said distal section are removably interconnected.

16. A bone anchor insertion device according to claim 13, wherein said driver is removably interconnected to said distal section.

17. A bone anchor insertion device according to claim 13, wherein said driver removably engages a bone anchor assembly, a screw, a shank, a tulip, or a combination thereof.

18. A bone anchor insertion device according to claim 13, wherein a stylet direction is rotatably controlled.

19. A bone anchor insertion device according to claim 13, wherein said distal section further comprises a lock.

20. A bone anchor insertion device according to claim 13, wherein said distal section further comprises a spring, piston, hydraulic component, an elastic component, a magnetic component, or any combination thereof.

* * * * *